(12) United States Patent
Korkeamäki et al.

(10) Patent No.: US 11,129,928 B2
(45) Date of Patent: Sep. 28, 2021

(54) ASSEMBLY FOR COLLECTING FLUID DURING A MEDICAL OR A SURGICAL OPERATION

(71) Applicant: Serres Oy, Kauhajoki As (FI)

(72) Inventors: Rami-Matti Korkeamäki, Kauhajoki (FI); Jarmo Mäkiranta, Kauhajoki (FI); Kimmo Frondelius, Kauhajoki (FI)

(73) Assignee: SERRES OY, Kauhajoki As (FI)

( * ) Notice: Subject to any disclaimer, the term of this patent is extended or adjusted under 35 U.S.C. 154(b) by 186 days.

(21) Appl. No.: 16/315,428

(22) PCT Filed: Jul. 6, 2017

(86) PCT No.: PCT/FI2017/050519
§ 371 (c)(1),
(2) Date: Jan. 4, 2019

(87) PCT Pub. No.: WO2018/007685
PCT Pub. Date: Jan. 11, 2018

(65) Prior Publication Data
US 2019/0307932 A1    Oct. 10, 2019

(30) Foreign Application Priority Data

Jul. 6, 2016    (FI) ..................... 20165567

(51) Int. Cl.
*A61M 1/00*    (2006.01)
*A61M 39/22*    (2006.01)
(Continued)

(52) U.S. Cl.
CPC ........ *A61M 1/0017* (2014.02); *A61M 1/0001* (2013.01); *A61M 1/0023* (2013.01);
(Continued)

(58) Field of Classification Search
CPC ........ A61M 1/00; A61M 39/22; A61M 39/24; A61M 13/02; A61M 27/00; A61F 13/00; A61B 17/50
See application file for complete search history.

(56) References Cited

U.S. PATENT DOCUMENTS 3,211,144 A    10/1965 Nehring
3,478,743 A    11/1969 Ericson
(Continued)

FOREIGN PATENT DOCUMENTS

CA    1168539 A    6/1984
CN    2604585 Y    2/2004
(Continued)

OTHER PUBLICATIONS

First Notification of Office Action dated Sep. 2, 2020, by the Chinese Patent Office in corresponding Chinese Patent Application No. 201780041920.X, and an English Translation of the Office Action. (14 pages).

(Continued)

*Primary Examiner* — Tatyana Zalukaeva
*Assistant Examiner* — Ilya Y Treyger
(74) *Attorney, Agent, or Firm* — Buchanan Ingersoll & Rooney PC

(57) ABSTRACT

An assembly is disclosed for collecting fluid during a medical or a surgical operation. The assembly can include a canister having an openable lid and a collection liner. The collection liner can include a closed bag portion and an inlet for a collection container. The inlet has a first end and a second end, which opens into the bag portion. The bag portion is placed inside the canister. The first end of the inlet for a collection container extends from between the edge of the canister and the edge of the lid to the outside of the canister when the lid is closed.

12 Claims, 20 Drawing Sheets

(51) Int. Cl.
*A61M 39/24* (2006.01)
*G16H 40/63* (2018.01)
*A61M 27/00* (2006.01)
*A61F 13/00* (2006.01)

(52) U.S. Cl.
CPC ........ *A61M 1/0025* (2014.02); *A61M 1/0049* (2013.01); *A61M 1/0052* (2014.02); *A61M 1/0096* (2014.02); *A61M 39/22* (2013.01); *A61M 39/223* (2013.01); *A61M 39/24* (2013.01); *G16H 40/63* (2018.01); *A61M 2205/15* (2013.01); *A61M 2205/3393* (2013.01); *A61M 2205/502* (2013.01); *A61M 2205/587* (2013.01); *A61M 2205/60* (2013.01); *A61M 2205/6054* (2013.01); *A61M 2205/7536* (2013.01); *A61M 2209/082* (2013.01); *A61M 2209/084* (2013.01); *A61M 2209/086* (2013.01)

(56) References Cited

U.S. PATENT DOCUMENTS

| | | | |
|---|---|---|---|
| 3,556,101 A | 1/1971 | Economou | |
| 3,648,698 A | 3/1972 | Doherty | |
| 3,782,384 A | 1/1974 | Timmermans | |
| 3,848,628 A | 11/1974 | Durham et al. | |
| 4,404,924 A | 9/1983 | Goldberg et al. | |
| 4,449,969 A | 5/1984 | Schweizer | |
| 4,525,167 A | 6/1985 | Goldberg et al. | |
| 4,648,870 A | 3/1987 | Goldberg et al. | |
| 4,650,478 A | 3/1987 | Dunn | |
| 5,066,283 A | 11/1991 | Skrabal | |
| 5,185,007 A | 2/1993 | Middaugh et al. | |
| 5,203,769 A | 4/1993 | Clement et al. | |
| 5,238,582 A | 8/1993 | Hori et al. | |
| 5,248,275 A * | 9/1993 | McGrath | A63H 27/10 137/512.15 |
| 5,391,351 A | 2/1995 | Kaufman | |
| 5,589,145 A | 12/1996 | Kaufinan | |
| 5,776,118 A | 7/1998 | Seifert et al. | |
| 5,914,047 A | 6/1999 | Griffiths | |
| 5,945,004 A | 8/1999 | Ohira et al. | |
| 6,152,902 A | 11/2000 | Christian et al. | |
| 6,183,453 B1 | 2/2001 | Swisher | |
| 6,331,246 B1 | 12/2001 | Beckham et al. | |
| 6,679,529 B2 | 1/2004 | Johnson et al. | |
| 7,615,037 B2 | 11/2009 | Murray et al. | |
| 7,635,359 B2 | 12/2009 | Nakazawa et al. | |
| 7,674,039 B2 | 3/2010 | McMahon et al. | |
| 7,708,724 B2 * | 5/2010 | Weston | A61M 1/0031 604/304 |
| 8,118,796 B2 | 2/2012 | Rajamaki | |
| 8,202,002 B2 | 6/2012 | McMahon et al. | |
| 8,216,199 B2 | 7/2012 | Murray et al. | |
| 8,251,971 B2 | 8/2012 | Graf et al. | |
| 8,292,857 B2 | 10/2012 | Martini et al. | |
| 8,449,510 B2 | 5/2013 | Martini et al. | |
| 8,518,002 B2 | 8/2013 | Murray et al. | |
| 8,740,866 B2 | 6/2014 | Reasoner et al. | |
| 8,827,969 B2 | 9/2014 | Martini et al. | |
| 8,882,737 B2 | 11/2014 | Graf et al. | |
| 8,915,897 B2 | 12/2014 | Murray et al. | |
| 9,089,629 B2 | 7/2015 | Martini et al. | |
| 9,375,520 B2 | 6/2016 | Martini et al. | |
| 9,579,428 B1 | 2/2017 | Reasoner et al. | |
| 9,662,426 B2 | 5/2017 | Martini et al. | |
| 9,782,524 B2 | 10/2017 | Reasoner et al. | |
| 10,105,470 B2 | 10/2018 | Reasoner et al. | |
| 10,188,775 B2 | 1/2019 | Martini et al. | |
| 10,722,617 B2 | 7/2020 | Murray et al. | |
| 2001/0040123 A1 | 11/2001 | Beckham | |
| 2003/0213733 A1 | 11/2003 | Beckham et al. | |
| 2003/0225366 A1 | 12/2003 | Morgan et al. | |
| 2005/0244083 A1 | 11/2005 | McMahon et al. | |
| 2006/0079853 A1 | 4/2006 | Christensen et al. | |
| 2006/0276762 A1 | 12/2006 | Nakazawa et al. | |
| 2007/0135778 A1 | 6/2007 | Murray et al. | |
| 2007/0135779 A1 | 6/2007 | Lalomia et al. | |
| 2009/0005747 A1 | 1/2009 | Michaels et al. | |
| 2009/0012485 A1 | 1/2009 | Michaels et al. | |
| 2009/0036847 A1 | 2/2009 | Rajamaki | |
| 2009/0101219 A1 | 4/2009 | Martini et al. | |
| 2010/0016825 A1 | 1/2010 | Graf et al. | |
| 2010/0036335 A1 | 2/2010 | Murray et al. | |
| 2010/0082016 A1 | 4/2010 | Graham | |
| 2010/0166341 A1 | 7/2010 | McMahon et al. | |
| 2011/0118680 A1 * | 5/2011 | Michaels | A47L 7/0038 604/317 |
| 2011/0272039 A1 | 11/2011 | Martini et al. | |
| 2011/0277851 A1 | 11/2011 | Martini et al. | |
| 2011/0278294 A1 | 11/2011 | Martini et al. | |
| 2011/0278295 A1 | 11/2011 | Martini et al. | |
| 2011/0278296 A1 | 11/2011 | Martini et al. | |
| 2012/0029448 A1 | 2/2012 | Ehlert | |
| 2012/0215187 A1 | 8/2012 | Tippet et al. | |
| 2012/0238975 A1 | 9/2012 | Murray et al. | |
| 2013/0071048 A1 | 3/2013 | Graf et al. | |
| 2013/0090614 A1 | 4/2013 | Christensen et al. | |
| 2013/0144232 A1 | 6/2013 | Michaels et al. | |
| 2013/0247326 A1 | 9/2013 | Michaels et al. | |
| 2013/0341330 A1 | 12/2013 | Michaels et al. | |
| 2013/0345651 A1 | 12/2013 | Michaels et al. | |
| 2013/0345652 A1 | 12/2013 | Murray et al. | |
| 2014/0171887 A1 | 6/2014 | Smith et al. | |
| 2014/0343515 A1 | 11/2014 | Sylvester et al. | |
| 2014/0358095 A1 | 12/2014 | Christensen et al. | |
| 2015/0105740 A1 | 4/2015 | Reasoner et al. | |
| 2015/0224237 A1 | 8/2015 | Reasoner et al. | |
| 2015/0306285 A1 | 10/2015 | Sylvester et al. | |
| 2015/0328379 A1 | 11/2015 | Carr et al. | |
| 2016/0038665 A1 | 2/2016 | Schaefer et al. | |
| 2016/0166742 A1 | 6/2016 | Layser et al. | |
| 2016/0206791 A1 | 7/2016 | Christensen et al. | |
| 2016/0235962 A1 | 8/2016 | Gebauer | |
| 2017/0043064 A1 | 2/2017 | Reasoner et al. | |
| 2017/0043068 A1 | 2/2017 | Reasoner et al. | |
| 2017/0106127 A1 | 4/2017 | Chang et al. | |
| 2017/0246358 A1 | 8/2017 | Martini et al. | |
| 2017/0304511 A1 | 10/2017 | Harpham et al. | |
| 2018/0043081 A1 | 2/2018 | Lura et al. | |
| 2018/0243487 A1 | 8/2018 | Murray et al. | |
| 2018/0256790 A1 | 9/2018 | Murray et al. | |
| 2018/0264181 A1 | 9/2018 | Gregory et al. | |
| 2018/0361033 A1 | 12/2018 | Reasoner et al. | |
| 2019/0167870 A1 | 6/2019 | KorkeamÄki et al. | |
| 2019/0231941 A1 | 8/2019 | Frondelius | |
| 2019/0247554 A1 | 8/2019 | Frondelius et al. | |
| 2019/0269833 A1 | 9/2019 | Murray et al. | |
| 2019/0307931 A1 | 10/2019 | Frondelius et al. | |
| 2020/0179577 A1 | 6/2020 | KorkeamÄki et al. | |

FOREIGN PATENT DOCUMENTS

| | | | |
|---|---|---|---|
| CN | 1802180 A | | 7/2006 |
| CN | 1891579 A | | 1/2007 |
| CN | 101370535 A | | 2/2009 |
| CN | 102514803 A | | 6/2012 |
| CN | 104936631 A | | 9/2015 |
| EP | 0040427 A1 | | 11/1981 |
| EP | 0068744 A1 | | 1/1983 |
| EP | 0390094 A1 | | 10/1990 |
| EP | 0668084 A1 | | 8/1995 |
| EP | 1398018 A1 | | 3/2004 |
| EP | 1642603 A1 | | 4/2006 |
| EP | 2168611 A1 | | 3/2010 |
| GB | 2249613 A | | 5/1992 |
| GB | 1 642 603 | * | 4/2006 |
| JP | H02157083 A | | 6/1990 |
| JP | H0347257 A | | 2/1991 |
| JP | 2003519460 A | | 6/2003 |
| JP | 2003526381 A | | 9/2003 |
| JP | 2009519776 A | | 5/2009 |
| JP | 2009-526556 A | | 7/2009 |

(56) References Cited

FOREIGN PATENT DOCUMENTS

| | | |
|---|---|---|
| JP | 2010540193 A | 12/2010 |
| JP | 5800440 B1 | 9/2015 |
| JP | 2015532194 A | 11/2015 |
| WO | 8002706 A1 | 12/1980 |
| WO | 97/27883 A1 | 8/1997 |
| WO | 9745055 A1 | 12/1997 |
| WO | 9900154 A1 | 1/1999 |
| WO | 0114048 A1 | 3/2001 |
| WO | 0149344 A1 | 7/2001 |
| WO | 2005079947 A2 | 9/2005 |
| WO | 2007079319 A2 | 7/2007 |
| WO | 2008118397 A1 | 10/2008 |
| WO | 2008144951 A1 | 12/2008 |
| WO | 2009046403 A1 | 4/2009 |
| WO | 2014/093984 A1 | 6/2014 |
| WO | 2015134749 A2 | 9/2015 |
| WO | 2015/173980 A1 | 11/2015 |
| WO | 2017007660 A1 | 1/2017 |
| WO | 2017066798 A1 | 4/2017 |

OTHER PUBLICATIONS

Ca-Mi Srl: "CA-MI Catalogue 2014 Surgical Suction Units Suction Devices", Nov. 30, 2013, XP055413037, Retrieved from the Internet: URL:http://www.medicalsuction.co.uk/media/pdf/CAMI surgical suction line.pdf.
Ca-Mi Srl: 11 Catalogue 2013: Suction Line, Oct. 26, 2012, XP055413982, Retrieved from the Internet: URL:http://pdf.medicalexpo.com/pdf/ca-mi/ca-mi-suction-units-general-catalogue-2013/80188-104133.html.
International Preliminary Report on Patentability (PCT/IPEA/409) dated Oct. 15, 2018, by the European Patent Office as the International Preliminary Examining Authority for International Application No. PCT/FI2017/050509.
International Preliminary Report on Patentability (PCT/IPEA/409) dated Oct. 15, 2018, by the European Patent Office as the International Preliminary Examining Authority for International Application No. PCT/FI2017/050519.
International Preliminary Report on Patentability (PCT/IPEA/409) dated Oct. 17, 2018, by the European Patent Office as the International Preliminary Examining Authority for International Application No. PCT/FI2017/050522.
International Preliminary Report on Patentability (PCT/IPEA/409) dated Oct. 2, 2018, by the European Patent Office as the International Preliminary Examining Authority for International Application No. PCT/FI2017/050521.
International Preliminary Report on Patentability (PCT/IPEA/409) dated Oct. 8, 2018, by the European Patent Office as the International Preliminary Examining Authority for International Application No. PCT/FI2017/050514.
International Preliminary Report on Patentability (PCT/IPEA/409) dated Oct. 8, 2018, by the European Patent Office as the International Preliminary Examining Authority for International Application No. PCT/FI2017/050517.
International Search Report (PCT/ISA/210) dated Oct. 10, 2017, by the European Patent Office as the International Searching Authority for International Application No. PCT/FI2017/050519.
International Search Report (PCT/ISA/210) dated Oct. 16, 2017, by the European Patent Office as the International Searching Authority for International Application No. PCT/FI2017/050517.
International Search Report (PCT/ISA/210) dated Oct. 2, 2017, by the European Patent Office as the International Searching Authority for International Application No. PCT/FI2017/050509.
International Search Report (PCT/ISA/210) dated Oct. 20, 2017, by the European Patent Office as the International Searching Authority for International Application No. PCT/FI2017/050522.
International Search Report (PCT/ISA/210) dated Oct. 23, 2017, by the European Patent Office as the International Searching Authority for International Application No. PCT/FI2017/050521.
International Search Report (PCT/ISA/210) dated Oct. 24, 2017, by the European Patent Office as the International Searching Authority for International Application No. PCT/FI2017/050514.
Search Report dated Feb. 24, 2017, by the Finnish Patent Office for Application No. 20165567.
Written Opinion (PCT/ISA/237) dated Oct. 10, 2017, by the European Patent Office as the International Searching Authority for International Application No. PCT/FI2017/050519.
Written Opinion (PCT/ISA/237) dated Oct. 16, 2017, by the European Patent Office as the International Searching Authority for International Application No. PCT/FI2017/050517.
Written Opinion (PCT/ISA/237) dated Oct. 2, 2017, by the European Patent Office as the International Searching Authority for International Application No. PCT/FI2017/050509.
Written Opinion (PCT/ISA/237) dated Oct. 20, 2017, by the European Patent Office as the International Searching Authority for International Application No. PCT/FI2017/050522.
Written Opinion (PCT/ISA/237) dated Oct. 23, 2017, by the European Patent Office as the International Searching Authority for International Application No. PCT/FI2017/050521.
Written Opinion (PCT/ISA/237) dated Oct. 24, 2017, by the European Patent Office as the International Searching Authority for International Application No. PCT/FI2017/050514.
Office Action (First Notification of Office Action) dated Nov. 24, 2020, by the Chinese Patent Office in corresponding Chinese Patent Application No. 201780041893.6, and an English Translation of the Office Action. (16 pages).
Office Action dated Sep. 27, 2020, issued in the corresponding Chinese Patent Application No. 201780041922.9, 15 pages including 8 pages of English translation.
Office Action dated Dec. 17, 2019, issued in the corresponding Japanese Patent Application No. 2019500389, 9 pages including 4 pages of English translation.
Office Action dated Nov. 27, 2019, issued in the corresponding Japanese Patent Application No. 2019500492, 6 pages including 3 pages of English translation.
Office Action dated Nov. 28, 2019, issued in the corresponding Japanese Patent Application No. 2019500493, 8 pages including 4 pages of English translation.
Office Action dated Jul. 22, 2020, issued in the corresponding Japanese Patent Application No. 2019500493, 9 pages including 4 pages of English translation.
Non Final Office Action dated Jan. 22, 2021, by the U.S. Patent and Trademark Office in U.S. Appl. No. 16/315,341, 12 pages.
Non Final Office Action dated Mar. 26, 2021, by the U.S. Patent and Trademark Office in U.S. Appl. No. 16/315,297, 28 pages.
Office Action dated Nov. 24, 2020, by the U.S. Patent and Trademark Office in U.S. Appl. No. 16/315,202, 16 pages.
Office Action dated Jan. 28, 2021, by the U.S. Patent and Trademark Office in U.S. Appl. No. 16/315,262, 8 pages.
Office Action dated Mar. 15, 2021, by the U.S. Patent and Trademark Office in U.S. Appl. No. 16/315,224, 8 pages.
Second Notification of Office Action dated Apr. 8, 2021, by the Chinese Patent Office in corresponding Chinese Patent Application No. 201780041920, and an English Translation of the Office Action. (14 pages).
Office Action (Communication) dated Apr. 8, 2021, by the European Patent Office in corresponding European Patent Application No. 17743373.7. (7 pages).
Office Action (Rejection) dated Jun. 18, 2021, by the U.S. Patent Office in co-pending U.S. Appl. No. 16/315,262.
Office Action (Final Rejection) dated Jul. 8, 2021, by the Patent and Trademark Office in U.S. Appl. No. 16/315,202.
Office Action dated Jul. 20, 2021, by the U.S Patent and Trademark Office in U.S. Appl. No. 16/315,224.

* cited by examiner

ASSEMBLY FOR COLLECTING FLUID DURING A MEDICAL OR A SURGICAL OPERATION

BACKGROUND OF THE INVENTION

The present invention relates to an assembly for collecting fluid during a medical or a surgical operation. The assembly comprises a canister having an openable lid and a collection liner comprising a closed bag portion and an inlet for a collection container. The inlet has a first end and a second end, which opens into the bag portion. The bag portion is placed inside the canister.

Known assemblies comprise either a canister without a lid, or a canister with a lid. When the canister is without the lid the collection liner has a lid. As the collection liner is disposable the material loss in manufacturing the lids is remarkable. The empty collection liners require a lot of space. They are inconvenient to assemble. The volume of the collection liners is limited because it is difficult to handle them when they are full.

When the canister is with the lid the collection container tube must be assembled and disassembled through the lid. The tube must be threaded through the lid, or the tube must be removed before opening the lid. It makes the handling of the disposable collection liner and the disposable tube troublesome. During disassembling the joints of the system one may be exposed to infectious liquid.

BRIEF DESCRIPTION OF THE INVENTION

The object of the invention is to provide a new type of a solution. The invention is characterized by the features of the independent claims. Some embodiments are disclosed in the dependent claims.

The collection container tube is not required to be disconnected from the collection liner while the collection liner is removed from the canister. It makes easier to handle the collection liner and the collection container tube. Further, less material is required for manufacturing of the disposable collection liners. As the canisters are reusable there is real saving in material.

Furthermore, the collection container tube can be disconnected from its other end. According to one embodiment the collection liner may have a site for connecting the disconnected end of the tube. If there are fluid drops in the tube they cannot leak out because both ends of the tube are closed.

The collection liner comprises a bag portion and a rigid handle. The bag portion is made of a flexible plastic material. The bag portion may be formed of a tubular plastic film. One end of the plastic film, i.e. the bottom of the bag portion, is closed by sealing the edges of the plastic film together, while at its other end the tubular plastic film is fixedly fastened e.g. by welding to the handle in such a manner that the bag portion forms a closed space with the handle.

The bottom of the bag portion may have a dual seam in such a manner that there are two seams having a distance between each other. An opening can be formed between the two seams, thereby forming an ancillary handle for helping to lift the collection liner. The opening can be, for example, a hole or a slit.

The ancillary handle enhances the possibility to lift the collection liner with both hands, i.e. one can take a grip with one hand from the handle and with the other hand from the ancillary handle. This property is important because the volume of the collection liner may be large.

The handle comprises the inlets that are necessary for the operation of the suction process. The handle may be a bar from which the collection liner is comfortable to lift. There are inlets for vacuum and a collection container tube in the bar. The inlets advance inside the bar and branch from the bar, thus advancing into the bag portion. The inlet for the vacuum has a lateral branch which is a channel for transmitting negative pressure outside the collection liner. Further, there may be an additional inlet in the handle for solidifying agent. The term solidifying agent is used throughout this text according to the main use but the inlet can be used to introduce any other chemical additive, such as a disinfectant or an anticoagulant.

All the inlets are secured so that the fluid inside the collection liner cannot leak out from it when the collection liner is removed. The inlets may be secured in such a manner that each inlet is provided with a back flow preventing means, i.e. a back flow preventing device. There may be a hydrophobic filter in the vacuum interface of the liner. The filter prevents fluid to advance into the vacuum tubing of the apparatus. The hydrophobic filter is made of a material which swells if the liquid meets the filter, thus blocking the flow.

The inlet for the liquid collected from a patient, i.e. the inlet for the collection container tube, may be provided with a no-return valve. The no-return valve may be a tube made of a thin plastic film. The tube surrounds the mouth of the inlet and it is fastened at the one end to the inlet and the other end is open. The thin plastic tube is open only when the pressure inside the tube is higher than around it.

The inlet of the solidifying agent, if it exists in the collection liner, may be provided with the same kind of no-return valve as the inlet for the collection container tube.

An important embodiment is to use the collection liner with an apparatus for collecting fluid from a patient and thus, the apparatus is described below. The main use of the apparatus is to collect fluid from the patient but the apparatus can be used to collect fluid from the operating site in general, e.g. from the floor of the operating theatre.

The apparatus for collecting fluid from a patient may comprise a one-piece structure or a two-piece structure. The two-piece structure comprises a control unit and a movable cart. The control unit and the movable cart are attachable to each other, i.e. when the surgical operation is going on and liquid is collected from the patient, the control unit and the cart are attached together by a locking means. After and before the operation the control unit and the movable cart can be used as separate units. At least the cart is movable and may have, for example, wheels but also the control unit may be movable and it may have wheels as well. The cart includes parts which are in contact with the collected liquid and thus, the movable cart improves the work flow between patients. One can use more than one interchangeable movable cart with the control unit and change the used cart to a cleaned one before a new patient.

The apparatus for collecting liquid from a patient may have an external vacuum source, i.e. the apparatus exploits, for example, the vacuum system of the hospital, or the apparatus may have an internal vacuum source, i.e. the apparatus has its own vacuum source, such as a vacuum pump. The internal vacuum source is preferably located in the control unit. The vacuum of the collection containers is regulated by internal vacuum regulators which are preferably located in the control unit.

The control unit and the movable cart are attached to each other by using connection plates. The vacuum lines between the control unit and the movable cart are automatically connected at the same time as well as the electrical connections between the control unit and the cart. The plates are drawn to each other by using negative pressure, i.e. vacuum. There is a separate valve for that operation. The valve is turned on when the control unit and the movable cart are sensed to be together, i.e. the valve is only turn on if the movable cart docks with the control unit and a locking means connecting the control unit and the movable cart is on.

The movable cart comprises positions for collection containers inside which the liquid flows. The collection containers may be disposable collection liners and they may be used with canisters inside which they are assembled. However, it is also possible that there are no collection liners and the liquid flows directly in the canisters, i.e. the canister is the collection container. The collection containers may be connected to one or more independent suction channels. Usually the apparatus comprises at least two independent suction channels.

A manifold comprises a housing, ports for patient tubes and ports for collection container tubes. The patient tube leads from the suction site or the operating site to the manifold and the collection container tube leads from the manifold to the collection container. Each port for connecting a patient is provided with a no-return valve which may be a thin plastic tube surrounding the port inside the housing. The plastic tube is open only when the pressure inside it is higher than around it.

Each port for the collection container tube may be provided with a valve. The valve may comprise, for example, a cylinder and a rotatable bar within each other. The cylinder may be provided with a hole and the rotatable bar may have a notch. When the bar is rotated the valve closes or opens depending on the fact whether the hole and the notch are on the same line, i.e. the port opens when the notch is parallel to the hole and the port shuts off when the notch is divergent to the hole. According to another alternative, the valve may comprise two cylinders provided with holes within each other. When the holes are on the same line the valve is open and when the holes are not on the same line the valve is closed.

The rotatable bar or the innermost cylinder may comprise at its end a form to which an actuator, such as a motor, grips. Each valve has an actuator which rotates the valves according to the parameters entered by the user. Thus, each valve is individually operable, i.e. the valve can be opened or closed individually.

When liquid is collected from the patient a tube is connected to the patient tube port and the collection container tube is connected to the port for the collection container tube. The liquid enters first to the housing of the manifold and after that it flows through an open port to a collection container.

When the suction is interrupted there is a possibility that fluid remains in the collection container tube. Further, negative pressure continues to prevail in the collection container. Therefore, the manifold may comprise by-pass channels in the ports for the collection container tubes. The aim of the channel is to remove fluid which remains in the collection container tube when the suction is interrupted and return the atmospheric pressure in the tube and in the collection container, i.e. the tube and the collection container reach the same pressure which prevails outside the apparatus. The channel, which opens to the outside of the port of the collection container tube, is open only when the port is closed.

The manifold may also comprise a by-pass channel in the housing of the manifold. There is a gasket between the housing and the channel. The negative pressure prevailing in the manifold can be measured from that channel by connecting the channel to a pressure sensor. The advantage of this measuring system is that liquid or aerosol in the housing of the manifold cannot penetrate into the channel although the manifold contains fluid and humid air and pressure in the manifold changes. The shape of the manifold is designed in such a manner that the by-pass channel is not hit by the fluid flow. The above-mentioned detail may be accomplished by protecting the mouth of the by-pass channel by at least one wall, preferably two walls on both sides of the mouth. A no-return valve may secure that liquid or aerosol are kept away from the channel in the case when pressure inside the manifold is higher than pressure in the by-pass channel. The measured negative pressure shows the pressure exerted to the patient. Further, it indicates together with flow measurement if there is a blockage in the system.

The by-pass channel may be choked and in contact with the atmospheric pressure. The choked contact to the atmospheric pressure guarantees that pressure in the measurement channel follows changes of the negative pressure in the manifold.

The manifold may be provided with an electronic identification system. For example, the electronic identification system may be an RFID tag comprising identification information about the manifold. The RFID tag comprises an integrated circuit containing the identification information and an antenna. The RFID tag is read with a reader and the information obtained from the reader controls the apparatus. If the identification information shows that the manifold is new the operation of the apparatus is allowable. If the identification information shows that the manifold has been used in the same operation the operation of the apparatus is also allowable. The above-mentioned case is possible, for example, if the manifold is unintentionally disconnected, or the manifold is transferred from one collection container to the other in order to increase capacity. Further, the manifold may be transferred from one suction channel of the apparatus to another suction channel of the apparatus during the same operation, or the manifold may be transferred from one cart to another cart used with the same control unit during the same operation. In both above-mentioned cases the operation of the apparatus is allowable. If the identification information shows that the manifold has been used before but not in the same operation the operation of the apparatus is prevented. However, if there are more than one suction channel in the apparatus other suction channels continue to function except the suction channel having the unacceptable manifold.

The collection liner may be used with a canister provided with an openable lid. The lid is hinged to the canister. The collection liner is placed inside the canister in such a manner that the vacuum is connected to the canister interior and the inlet for the collection container tube extends over the upper edge of the canister. After the collection liner is in its place in the canister, the lid of the canister is closed.

The lid comprises a gasket which seals the lid against the edge of the canister and the handle of the collection liner. The gasket may be a separate gasket or it may be an integral part of the lid, i.e. the lid is made of a material which is suitable for sealing, or the lid and the gasket are formed at the same time of different materials. In order to secure the lid in its place there is also a locking means which keeps the lid closed. As the inlet of the collection container tube extends over the edge of the canister, the inlet remains outside the canister when the lid is closed. Thus, the connection tube is not required to be disconnected from the liner while the collection liner is removed from the canister. The connection tube can be disconnected from its other end. The handle of the collection liner may have a site for connecting the disconnected end of the tube. Thus, if there are fluid drops in the tube they cannot leak out because both ends of the tube are closed.

The canisters may be connected to the cart via docking. The docking provides the mechanical mounting, the locking and the pneumatic connections between the cart and the canister. When the canister is unlocked the use of the canister is prevented.

In normal use, the liquid volume is detected by measuring the weight of the collection container. As the system detects the weight of the container, the container is not filled up to the level of vacuum inlet inside the liner preventing the hydrophobic filter getting in contact with liquid and therefore, the collection liner and the canister have essentially the same pressure level.

The collection liner engages to the negative pressure through a port in the canister, i.e. there is a connection provided with a gasket through the canister wall. The port may be provided with a flow meter. Together with the pressure measured from the manifold, the flow meter reveals reliably if there is a blockage in the system. If there is no flow or the flow value is under the predetermined range and the pressure measured from the manifold is higher than the regulated pressure there is a blockage in the apparatus, i.e. the absolute value of negative pressure is significantly lower in the manifold than the pressure led to the collection container. The pressure led to the collection container means the pressure that is intended to be used during the operation. In other words, if there is a weak flow and a poor suction there is a blockage. Accordingly, if there is a high flow and no significant negative pressure in the manifold but negative pressure led to the collection container is on or below a normal level, there is a leak in the apparatus.

In practice, a first pressure sensor measures a first pressure value which corresponds to the pressure value inside the manifold. A second pressure sensor measures a second pressure value in a channel leading negative pressure to the collection containers. The pressure difference of the first pressure value and the second pressure value is calculated.

The flow value has a predetermined range for each pressure difference. If the flow value is under the predetermined range compared to the predetermined range corresponding the pressure difference in question there is a blockage. If the flow value is over the predetermined range compared to the predetermined range corresponding the pressure difference in question there is a leak.

The control system of the apparatus may give an alarm and the display of the apparatus may show instructions for removing the blockage or the leakage. Further, it is possible to check the condition of the hydrophobic filter of the collection liner by measuring regulated negative pressure, negative pressure value in the manifold and the flow value. Thus, it is possible to predict clogging of the filter.

The canister or the cart may be provided with an optical indication means. The optical indication means may be illumination of the canister. Each canister may be provided with an illumination device. For example, a LED stripe may be fastened, preferably vertically, on a separation wall of the cart behind the canister. The illumination may be turned on when the canister is in use, or all canisters which are used during an operation may be illuminated. The intensity of the illumination may adjustable at each canister, or the illumination may be switched on/off at each canister. Alternatively, the optical indication means may be a film whose transparency can be changed, thereby showing the liquid only when desired. The film may be, for example, a film whose transparency changes when electricity is led to the film.

The collection containers have their predetermined positions in the movable cart. Each container is weighed during the suction to follow the amount of the collected liquid and the liquid inside the collection container. The amount of liquid that the collection container is allowed to receive is given beforehand, i.e. the user of the apparatus can choose how much liquid may enter into the collection container. The suction stops concerning the collection container in question when the predetermined amount has been reached. The suction and the consequent flow of fluid are directed automatically from the collection container which has reached the predetermined weight to another collection container. The change from the previous collection container to the following collection container takes place by closing the valve of the manifold through which the fluid has flown to the previous collection container and opening the valve of the manifold through which the fluid is going to flow to the following collection container.

The weighing can be made, for example, by using strain gauge transducers installed under the positions of the collection containers. The electrical resistance of the strain gauge transducer varies due to the load that is exerted to the transducer. On the basis of the resistance the weight of the collection container can be determined. There is an irrigation pole integrated to the control unit and a weighing unit receiving information from the weighing, i.e. the weighing unit measures the weight loss of the irrigation bag or bags if there are more than one bag hanging from the irrigation pole. Thereby one can obtain information about the amount of liquid that has been transferred to the operating site and the amount of liquid collected and thus, it is possible to calculate the liquid deficit. This information may have a clinical value. The weighing gives reliable results since the collection containers have a floating connection to the cart, i.e. the collection containers can move freely in respect of the cart. The collection containers are laterally supported but the weight of each container rests on the strain gauge transducer which is situated under the collection container.

The cart comprises a position for a cartridge and a reservoir containing solidifying agent. The vacuum in the collection container is used to move the solidifying agent from the reservoir to the collection container. The solidifying agent is inside the cartridge in such a manner that a user does not have to be in touch with the solidifying agent. The user just checks visually from outside whether there is enough solidifying agent in the reservoir and if not, she or he changes the cartridge for a full one. The cartridges are only for a single use. As the cartridge is put in its place in the movable cart the cartridge is opened automatically. The control unit monitors the amount of the solidifying agent dosages given from the cartridge and requests a new cartridge when required, i.e. the control unit detects the misuse of the apparatus. The cartridges may have radio frequency identification tags (RFID tags) on their surface and the control unit may identify the cartridges according to the identification information of the tags.

According to one alternative, the solidifying agent is fed in small doses into the collection container, i.e. the collection liner or the collection canister, during the suction process. The feeding process is automatic and it can be programmed so that a portion of the solidifying agent is fed, for example, after every half liter, on the surface of the liquid in the collection container. The system is useful, among others, in that that the liquid in the collection container solidifies as it flows inside the container. Further, the use of the solidifying agent is more precise and more effective compared to the known systems because the amount of the solidifying agent is in proportion with the amount of the collected liquid.

In practice, the cycle to form a portion of the solidifying agent may be as follows: There are at least three valves regulating the formation of the solidifying agent portion, namely the first valve, the second valve and the third valve. The first valve is the nearest valve to the collection container. The second valve exists between the first and the third valve. Between the second valve and the third valve there is the solidifying agent cartridge which opens via the reservoir into a tube leading to the collection container. In the beginning the first valve and the third valve are shut. The second valve is partially open. When the first valve is opened the vacuum starts to draw the solidifying agent out of the reservoir so that a portion of the solidifying agent is formed between the second valve and the third valve. In the next step, the first valve and the third valve are open and the second valve is still partially open. Air flows from the third valve which stops the flow of the solidifying agent and compacts the portion of the solidifying agent against the second valve.

In the following step all the valves are open. The portion of the solidifying agent is shot then into the collection container, thus solidifying the liquid in the collection container. After the portion is shot, the second valve and the third valve are closed in such a manner that the second valve remains half open as in the beginning of the process. The first valve is also eventually closed and the cycle to form the portion of the solidifying agent starts all over again.

Instead of the three valves described above, there may be a batching screw and valves, preferably two of them, for forming and releasing the dosage of the solidifying agent.

According to another alternative, the solidifying agent can be fed as loose powder without forming the above-mentioned compact dosage. The aim of this alternative is to distribute powder from the reservoir into the collection liner at known speed, i.e. certain amount of powder shall be released into the collection liner in certain time. The solidifying agent may be released, among others, after a certain volume of liquid is received in the collection container, after the collection container is full, after all the collection containers of the suction channel in question are full, the cart must be changed, or once the operation is completed. The suction process is interrupted during the discharge of the solidifying agent.

There are at least two valves, namely a liner valve and an air valve, which take part in giving out the solidifying agent. The liner valve is near to the collection container. The reservoir receiving solidifying agent from the cartridge is between the air valve and the liner valve. The pipe of the solidifying agent pipeline, which passes through the reservoir, may work as an ejector. The pipe may have an opening through which air flow grabs the solidifying agent. The opening is preferably on the underside of the pipe because under the pipe the powder is loose and easily movable. The lower part of the reservoir may be an inverted cone through which the pipe passes.

The liner valve and the air valve are open when the solidifying agent is distributed. The solidifying agent pipeline is in contact with ambient air through the air valve and it is in contact with vacuum through the liner valve. The pipe beyond the air valve may be choked in order to adjust the balance between ambient air and powder flowing in the pipe.

There may be a flush valve between the reservoir and the liner valve. The flush valve is opened at the end of the powder distribution when the air valve has been closed. The aim of the flush valve is that the flush valve opens access to ambient air and the air flow cleans the pipe from the powder residuals.

The port of the collection container tube in the manifold must be closed when the powder is distributed. In other words, the valve of the port of the collection container tube is closed.

The condition of the hydrophobic filter is important in this process because it may cause higher flow resistance than assumed. There may be a by-pass pipe provided with a choke in the collection container tube. The by-pass pipe is in contact with ambient air and it can be used to evaluate the condition of the hydrophobic filter of the collection liner. According to another alternative, the condition of the hydrophobic filter can be checked before the operation by using known parameters, i.e. pressure, air volume inside the collection container and response time to pressure changes.

Besides the apparatus described above, the collection liner may be used in an apparatus which is different from the apparatus described above. The collection liner may be used with the canister described above in an apparatus which is different from the apparatus described above. The collection container tube may be connected to a manifold, or directly to a device intended for a patient's treatment or waste collection.

A detached collection container may, for example, comprise a canister with a lid and a new type of collection liner with an inlet for a collection container tube. In this case the patient tube and the collection container tube are one and the same tube leading from the suction site to the collection container, i.e. there is no manifold between the patient tube and the collection container tube. In connection with the detached collection container may be used an external suction source, i.e. a stand-alone suction pump or a central vacuum system. The above mentioned suction system can be with or without the distribution of solidifying agent.

BRIEF DESCRIPTION OF THE DRAWINGS

In the following the solution will be described in greater detail by means of preferred embodiments with reference to the attached drawings, in which.

DETAILED DESCRIPTION OF SOME EMBODIMENTS

Figure 1A:
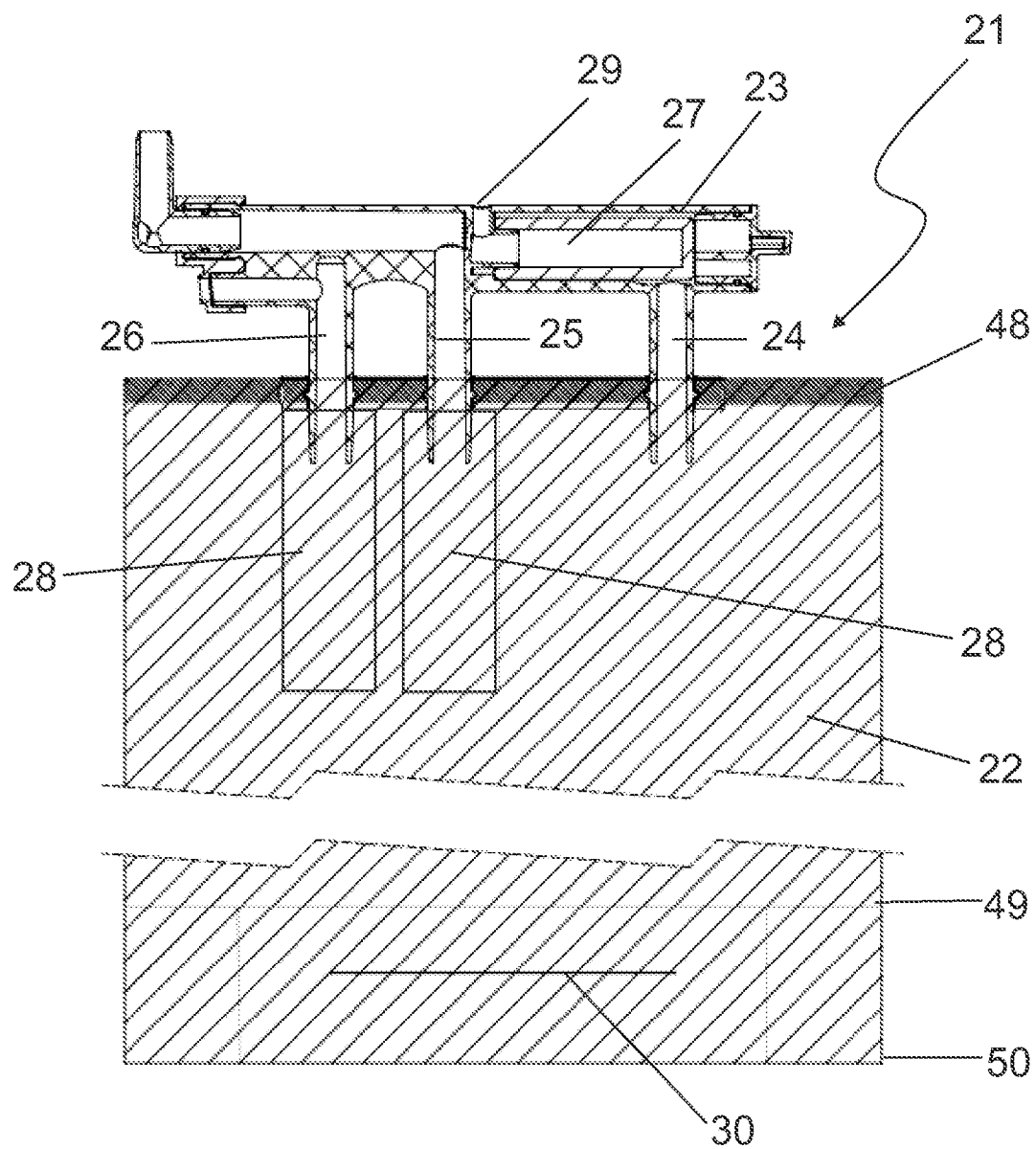
FIGS. 1a and 1b show a collection liner in a cross sectional view.

FIG. 1a shows a collection liner 21 as a cross sectional view. The collection liner comprises a closed bag portion 22 made of a flexible plastic film and a handle 23. The handle 23 serves as a handy grip but there are also functional channels inside the handle 23. The bag portion 22 and the handle 23 are attached to each other in such a manner that inlets 24, 25, 26, which advance inside the handle 23, open into the bag portion but otherwise the bag portion 22 is closed by a seam 48. The inlet 24 is for vacuum. The vacuum is connected to the collection liner 21 through a vacuum port 51 (shown in FIG. 3a). In the inlet 24 for the vacuum there is a hydrophobic filter 27 and an opening 29. The inlet 25 is for a collection container tube. The inlet 25 has a first end to which the collection container tube is joined and a second end which opens to the bag portion 22. The inlet 26 is for a solidifying agent or any other chemical additive entering into the collection liner 21.

Each inlet 24, 25, 26 is provided with a back flow preventing means, i.e. a back flow preventing device. The inlet 24 for vacuum comprises a hydrophobic filter 27 which swells if liquid reaches it, thus closing the flow. The inlet 25 for the collection container tube and the inlet 26 for the solidifying agent are surrounded with a thin plastic tube inside the bag portion 22. The thin plastic tube is fastened to the upper part of the bag portion 22, or it is fastened directly to the inlets. It forms a no-return valve 28. The no-return valve 28 is open only when the pressure inside the thin plastic tube is higher than around it. The thin plastic tube comprises of two parallel films joined together e.g. by welding. This structure cons firms that the plastic tube seals properly without openings in the edges.

There is an ancillary handle 30 at the bottom of the bag portion 22. The ancillary handle 30 may be a slit which is formed under a seam 49 which closes the bag portion 22. There may be another seam 50 which is parallel with the above-mentioned seam 49.

Figure 1B:
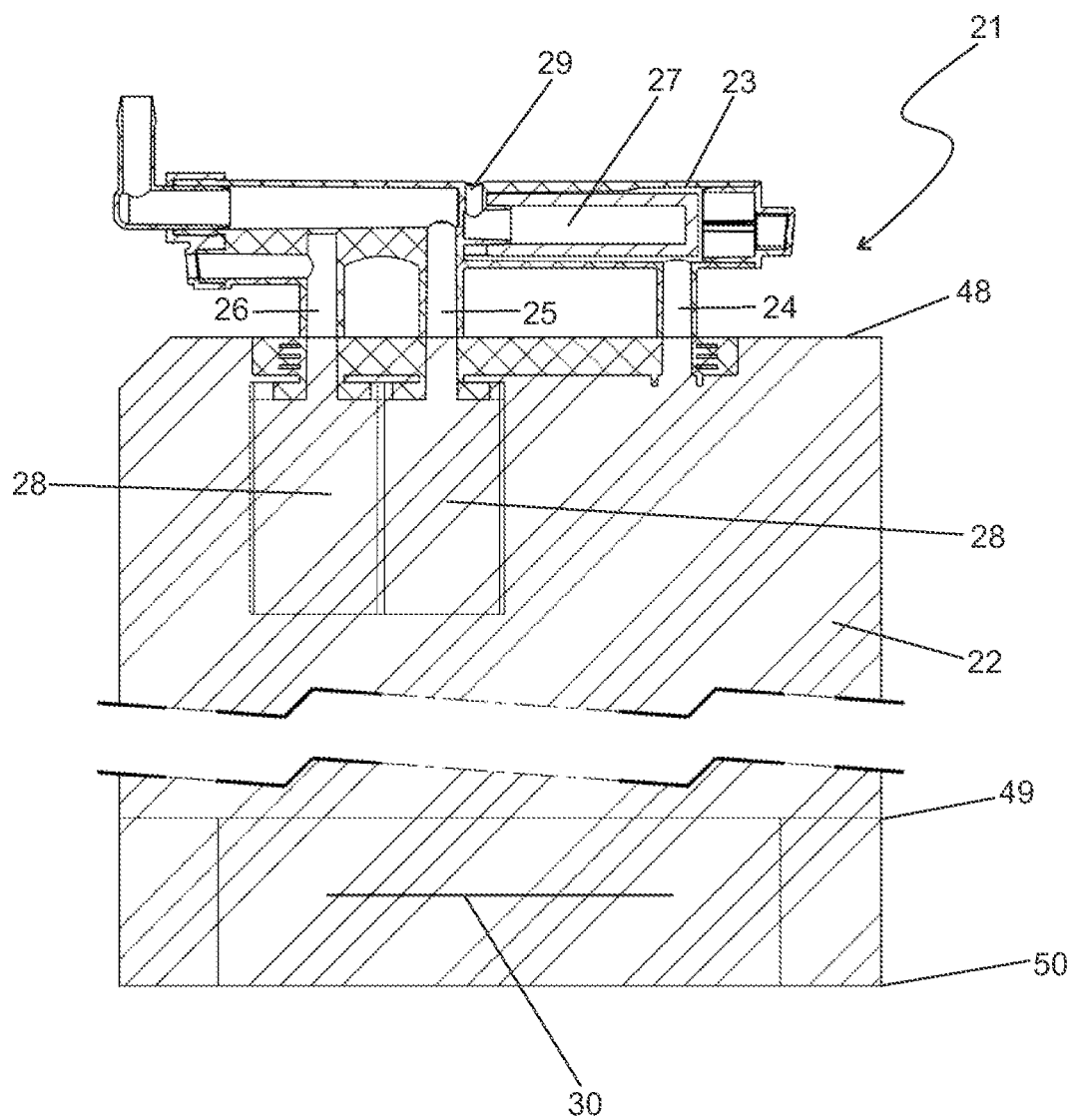

FIG. 1b shows a collection liner 21 as a cross sectional view. The solution of FIG. 1b differs from the solution of FIG. 1a in that that the thin plastic tubes, which form the no-return valves 28, are fastened directly to the inlets 25, 26.

Figure 1C:
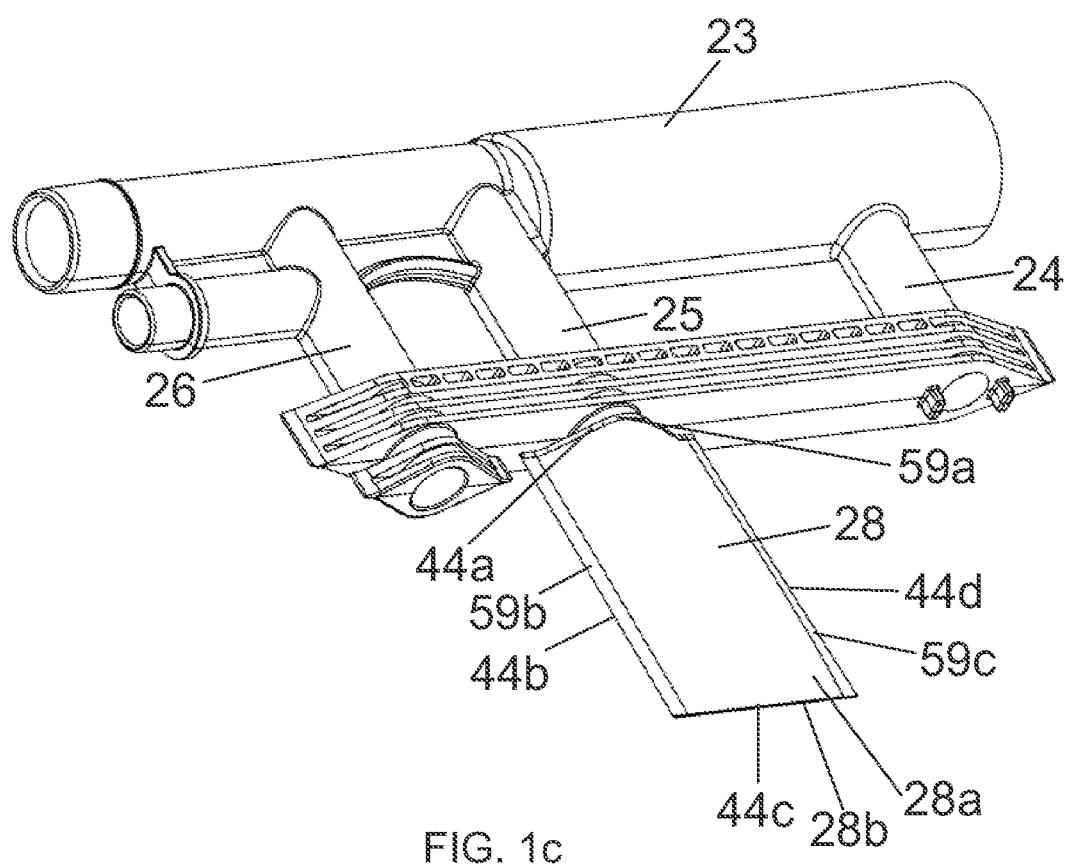
FIG. 1c shows a handle of a collection liner in a perspective view.

FIG. 1c shows a handle 23 of a collection liner 21 in a perspective view. The handle 23 comprises inlets 24, 25, 26. For the sake of clarity the inlet 26 is illustrated without a back flow preventing device, such as a no return valve, but the back flow preventing device consisting of a no return valve 28 is shown on the inlet 25. The same kind of no return valve 28 may exist in connection with the inlet 26.

The no return valve 28 comprises two thin plastic films 28a, 28b one upon the other. Both films 28a, 28b have the upper edge 44a, the lower edge 44c and the side edges 44b, 44d. The upper edges 44a of the films 28a, 28b are joined together and to the inlet 25 e.g. by welding so that a seam 59a forms. The respective side edges 44b, 44d are also joined together e.g. by welding in such a manner that seams 59b, 59c form. The lower edges 44c are not joined together, i.e. the lower end of the no return valve 28 is open. Thus, liquid is able to flow through the valve 28.

The seams 59b, 59c enhance the performance of the no return valve 28 because the films 28a, 28b are tightly together unless the pressure inside the thin plastic tube formed of the films 28a, 28b is higher than around it. Therefore, the collection container 21 is secured in such a manner that it cannot leak in any case.

Figure 2A:
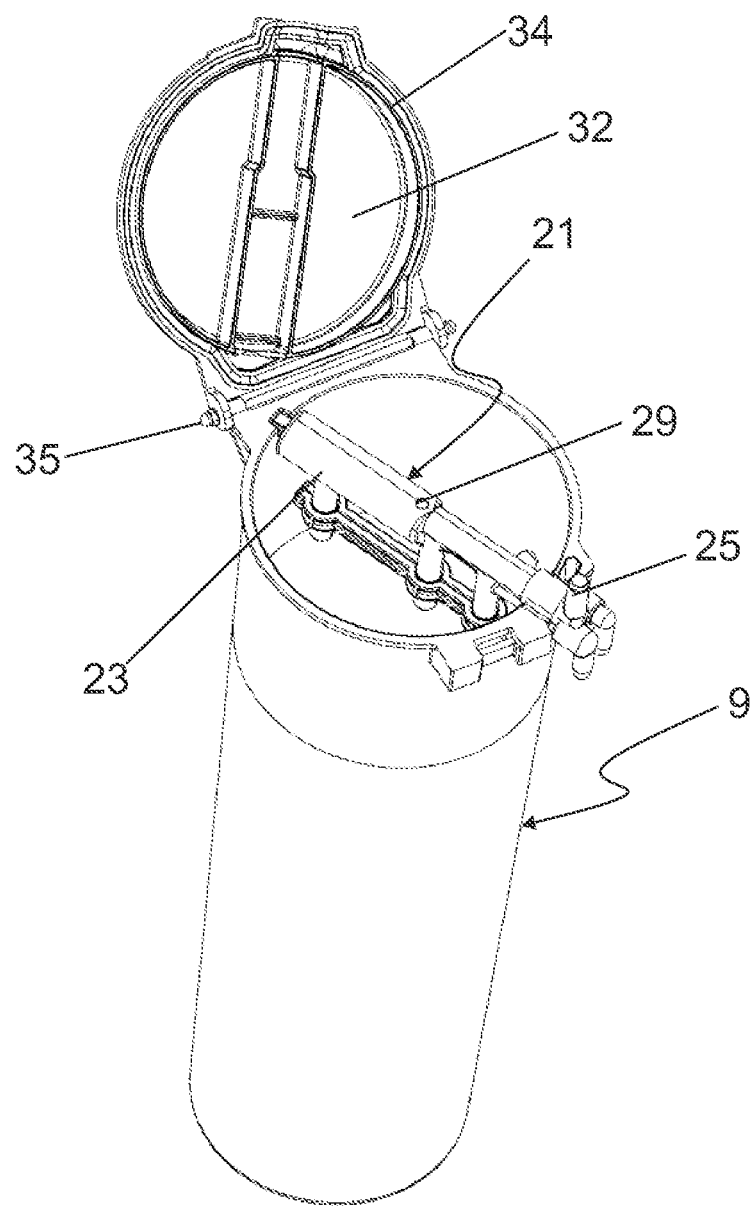
FIGS. 2a and 2b show a collection liner and a canister in a perspective view.

FIG. 2a shows one example of the use of the collection liner 21. The collection liner is used with a canister 9 having an openable lid 32. The lid 32 is attached to the canister 9 by a hinge 35. The collection liner 21 is placed inside the canister 9 in such a manner that the inlet 24 is connected via opening 29 to the internal space of the canister and the inlet 25 for the collection container tube extends over the upper edge of the canister 9. After the collection liner 21 is in its place in the canister 9, the lid 32 of the canister 9 is closed. The canister 9 comprises a latch (not shown) for the lid 32. The latch secures that the lid 32 stays closed and sealed until opened.

The lid 32 comprises a gasket 34 which tightens and seals the lid 32 and the handle 21 against the edge of the canister 9. The gasket 34 may be a separate gasket or it is an integral part of the lid 32 or the canister 9, i.e. the lid 32 or the canister 9 is made of a material which is suitable for sealing, or the lid 32 or the canister 9 and the gasket 34 are formed at the same time of different materials. As the inlet 25 of the collection container tube extends over the edge of the canister 9, the inlet 25 remains outside the canister 9 when the lid 32 is closed. Thus, the collection container tube is not required to be disconnected while the collection liner 21 is removed from the canister 9.

Figure 2B:
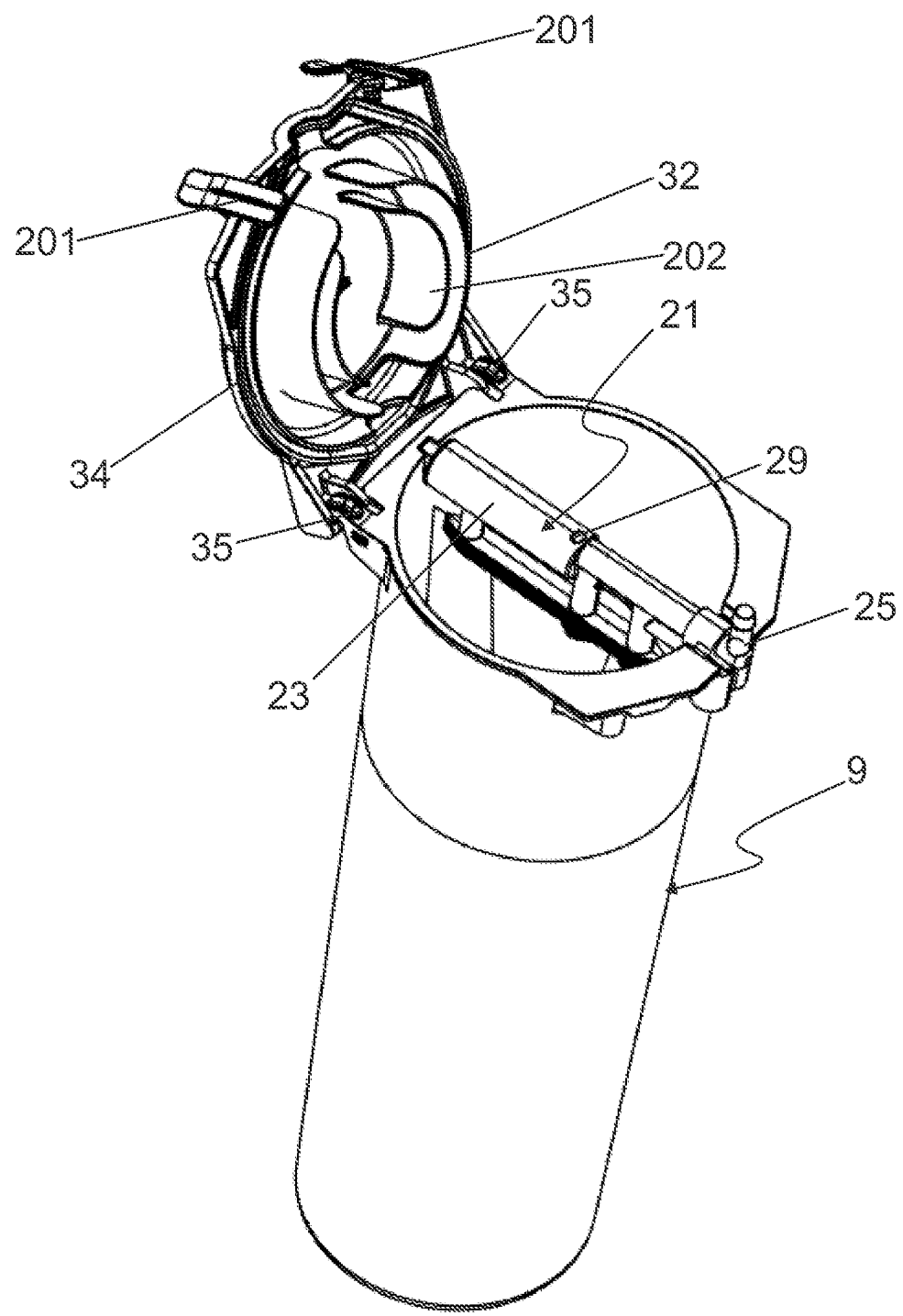

FIG. 2b shows another example of a collection liner and a canister in a perspective view. The collection liner 21 is used with a canister 9 having an openable lid 32. The lid 32 is attached to the canister 9 by hinges 35. It is possible to detach the lid 32 from the canister 9, which makes it easier to clean the canister 9 and the lid 32. The collection liner 21 is placed inside the canister 9 in such a manner that the inlet 24 is connected via opening 29 to the internal space of the canister and the inlet 25 for the collection container tube extends outside the canister 9. After the collection liner 21 is in its place in the canister 9, the lid 32 of the canister 9 is closed. The lid 32 comprises at least one latch 201 for the canister 9. The latch secures that the lid 32 stays closed and sealed until opened.

The lid 32 comprises curved guides 202 inside the lid 32. The curved guides are preferably concentric as shown in FIG. 2b. The aim of the guides 202 is to prevent the collection liner 21 to stretch too much.

Figure 3A:
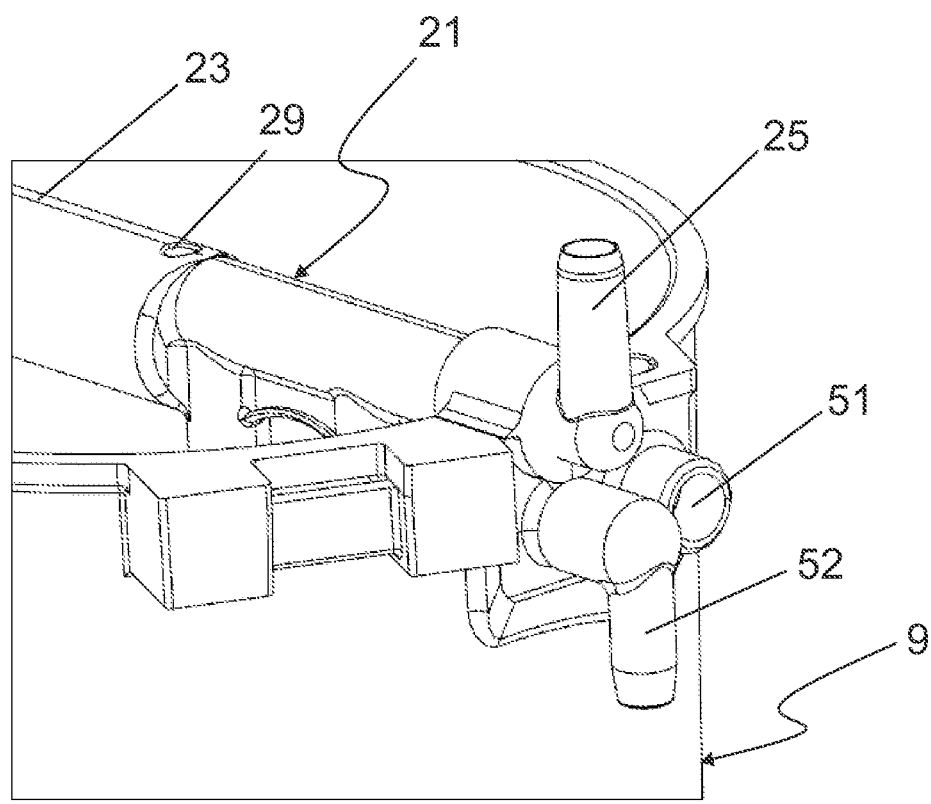
FIGS. 3a and 3b show a partial magnification of a collection liner and a canister in a perspective view.

FIG. 3a shows a partial magnification of a collection liner 21 and a canister 9. As seen in FIG. 3a, the inlet 25 of the collection container tube remains outside the periphery of the canister 9. The vacuum to the canister 9 is connected via a vacuum port 51. The solidifying agent or another additive is fed through a channel 52 to the inlet 26 (shown in FIG. 2a).

Figure 3B:
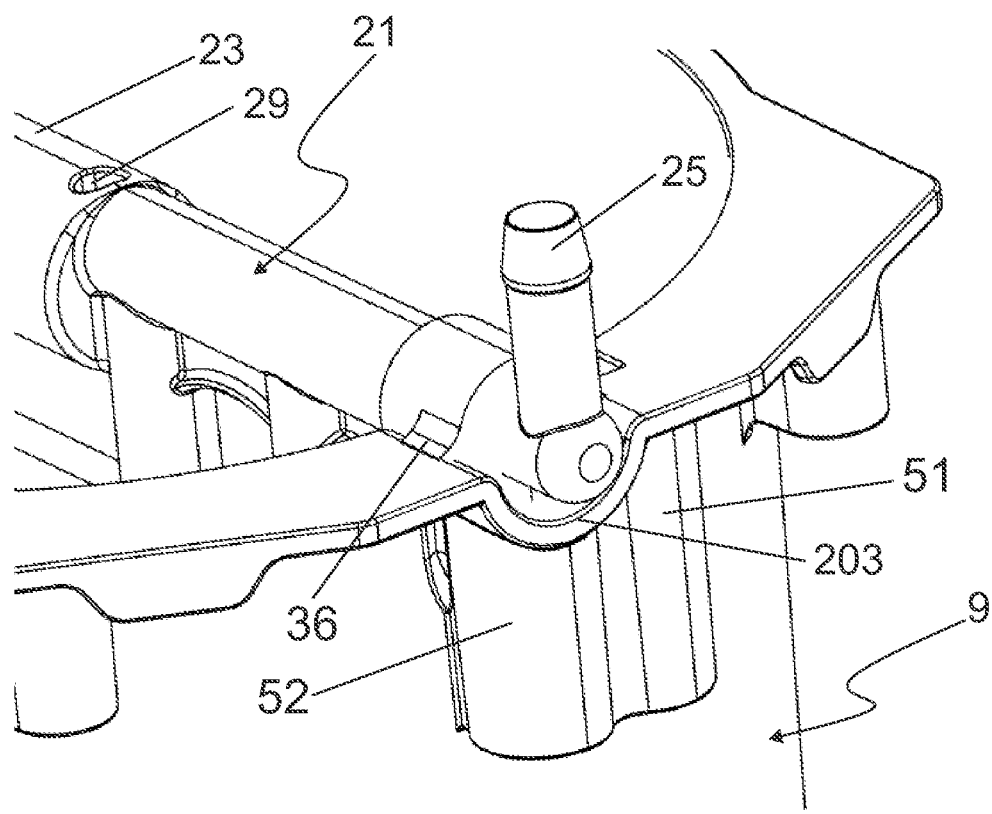

FIG. 3b shows a partial magnification of another solution comprising a collection liner 21 and a canister 9. As seen in FIG. 3b, the first end of the inlet 25 of the collection container tube is brought outside the canister 9. There is a recess 203 in the edge of the canister 9 which conforms to the outer shape of the handle 23. The handle 23 comprises a gasket 36 which seals the underside of the handle 23 towards the canister 9. The vacuum port is in the recess under the inlet 25.

Figure 3C:
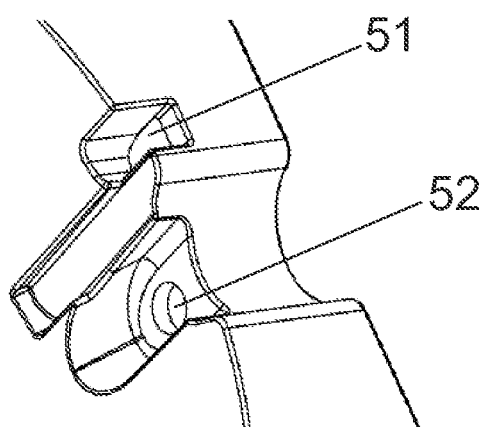
FIG. 3c shows a partial magnification of a canister from inside.

FIG. 3c shows a partial magnification of a collection liner from inside. One can see how the vacuum port 51 and the channel 52 are situated. The solidifying agent or another additive is fed through the channel 52 to the inlet 26. The channel 52 extends through the wall of the canister 9. The inlet 26 tightens against the channel 52, thus enabling the flow of the solidifying agent or another additive into the collection liner 21.

Figure 4A:
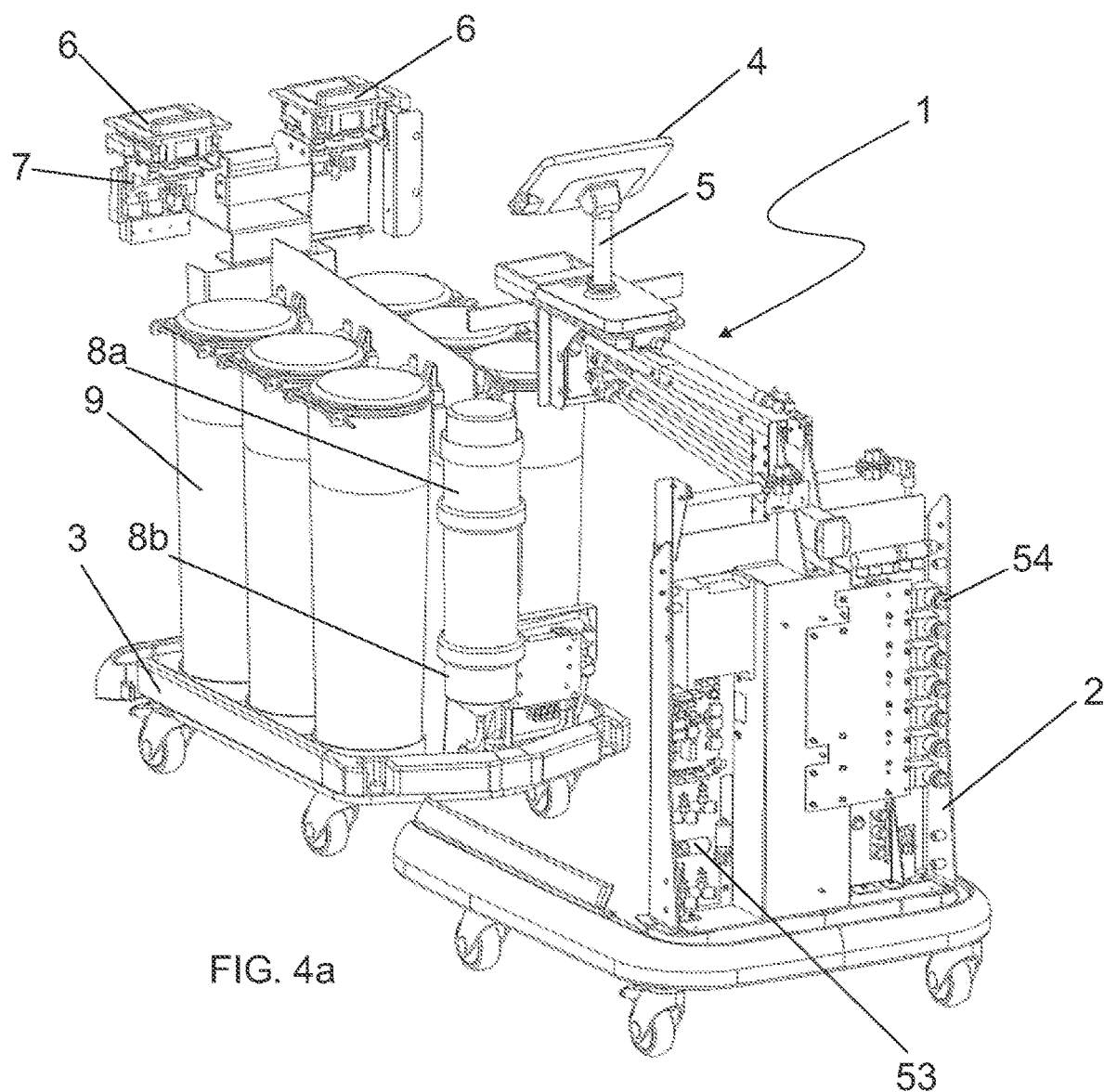
FIGS. 4a and 4b show an apparatus for collecting liquid from a patient in a perspective view.

FIG. 4a shows an apparatus 1 for collecting liquid from a patient. The collection liner 21 may be used, for example, in this apparatus. The apparatus 1 comprises a control unit 2 and a movable cart 3. The control unit 2 comprises a display unit 4, proportional valves 53 to control vacuum in the collection containers and valves 54 for collection container vacuum interfaces. The display unit 4 may comprise a touch screen acting both for displaying and for entering control parameters. The display unit 4 may be located on an arm 5 which turns around, i.e. the arm 5 allows the display to tilt and turn. On the movable cart 3 there are manifolds 6. Valves of the manifolds 6 are operated by suitable actuators, such as motors 7. The movable cart 3 comprises canisters 9 for collecting liquid, and a cartridge 8a and a reservoir 8b for a solidifying agent.

Figure 4B:
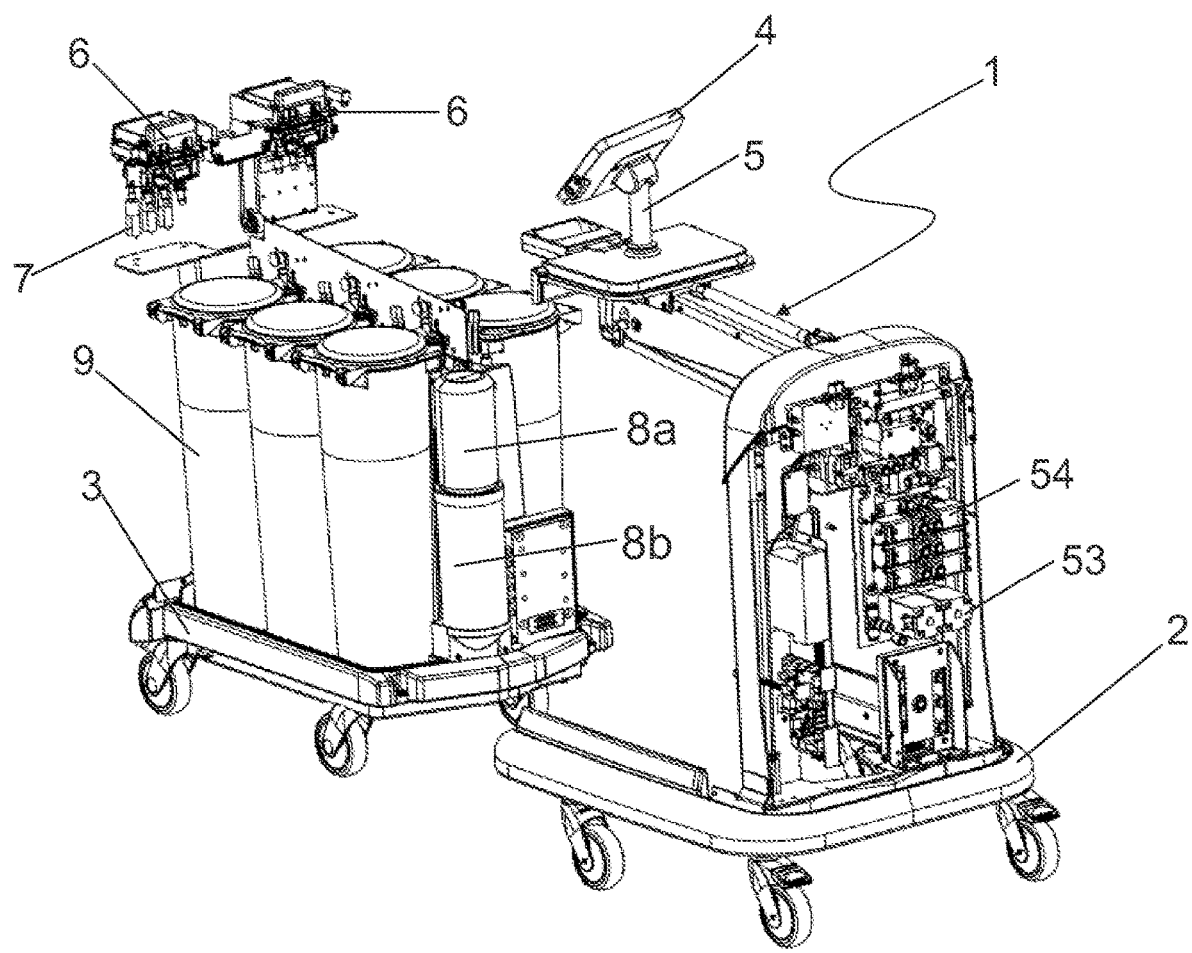

FIG. 4b shows one variation of the apparatus 1 described in connection with FIG. 4a.

Figure 5A:
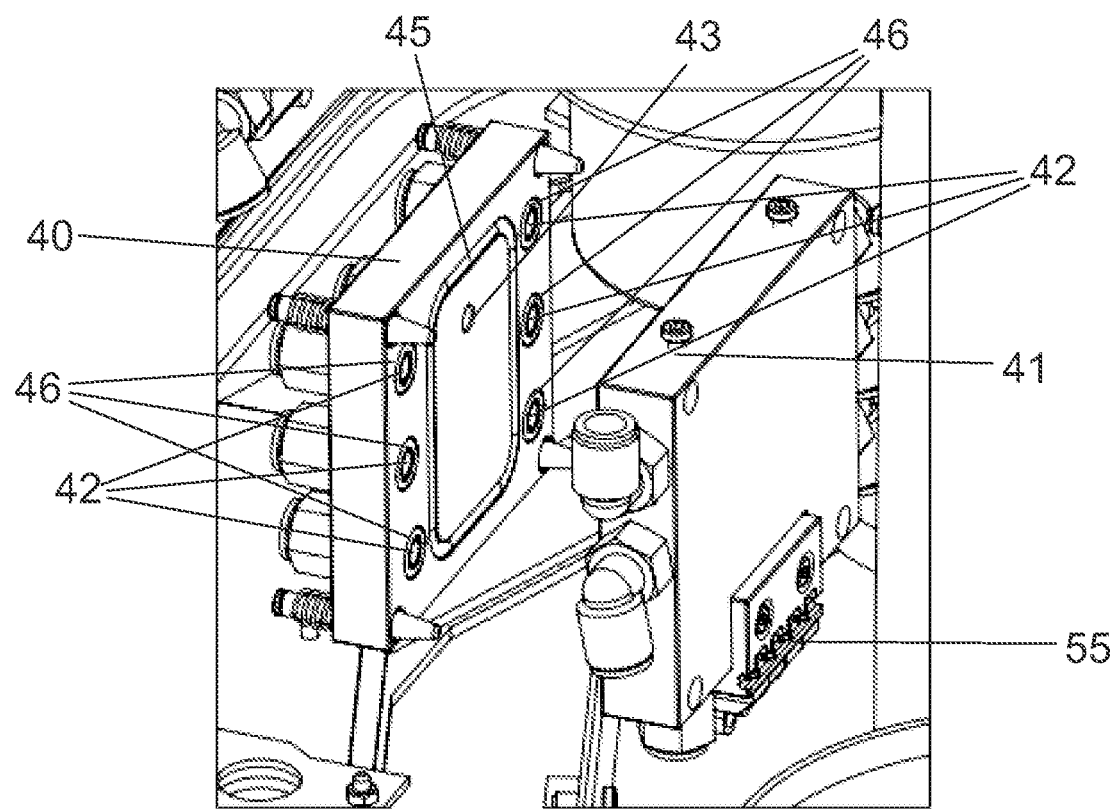
FIGS. 5a and 5b show a vacuum connection between a control unit and a movable cart in a perspective view.

FIG. 5a shows how vacuum and electrical couplings are made between the control unit 2 and the movable cart 3 in the apparatus 1. The control unit 2 and the movable cart 3 are attached to each other by using connection plates 40, 41. The vacuum lines 42 between the control unit 2 and the movable cart 3 are automatically connected at the same time. The plates 40, 41 are drawn to each other by negative pressure controlled by software via a dedicated valve connected between the plates through line 43. The valve connected to the line 43 is turned on when the control unit 2 and the movable cart 3 are sensed to be together. Thus, the valve is only turn on if the movable cart 3 docks with the control unit 2 and a locking means, which locks the control unit 2 and the movable cart 3 together, is on. The plates 40, 41 may be used as a mounting and an actuator for the electrical coupling 55 between the control unit 2 and the movable cart 3. There are also a gasket 45 and gaskets 46 around the vacuum lines 42.

Figure 5B:
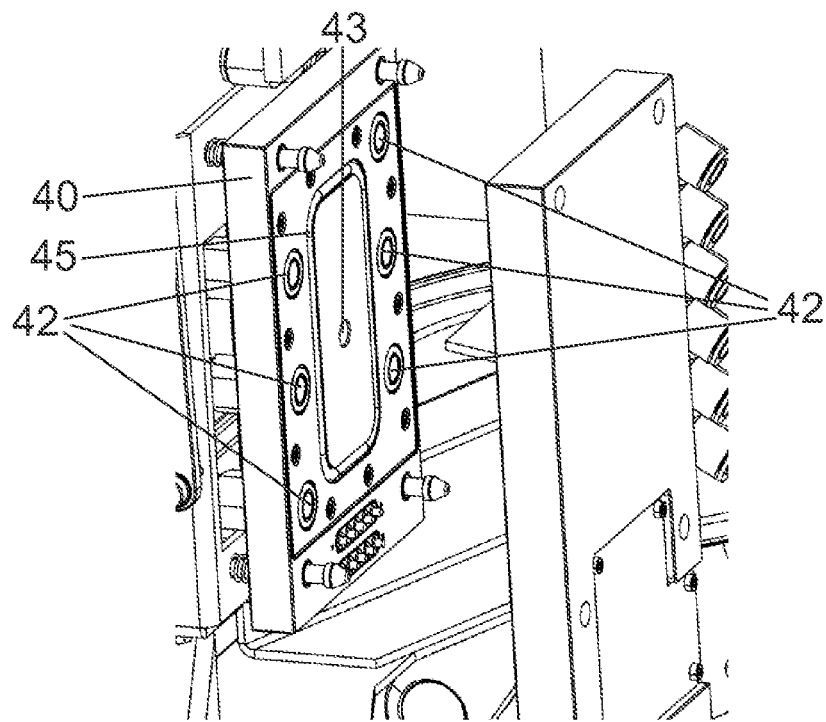

FIG. 5b shows another view how vacuum and electrical couplings are made between the control unit 2 and the movable cart 3 in the apparatus 1. The functioning of the system is basically the same as described in connection with FIG. 5a.

Figure 6A:
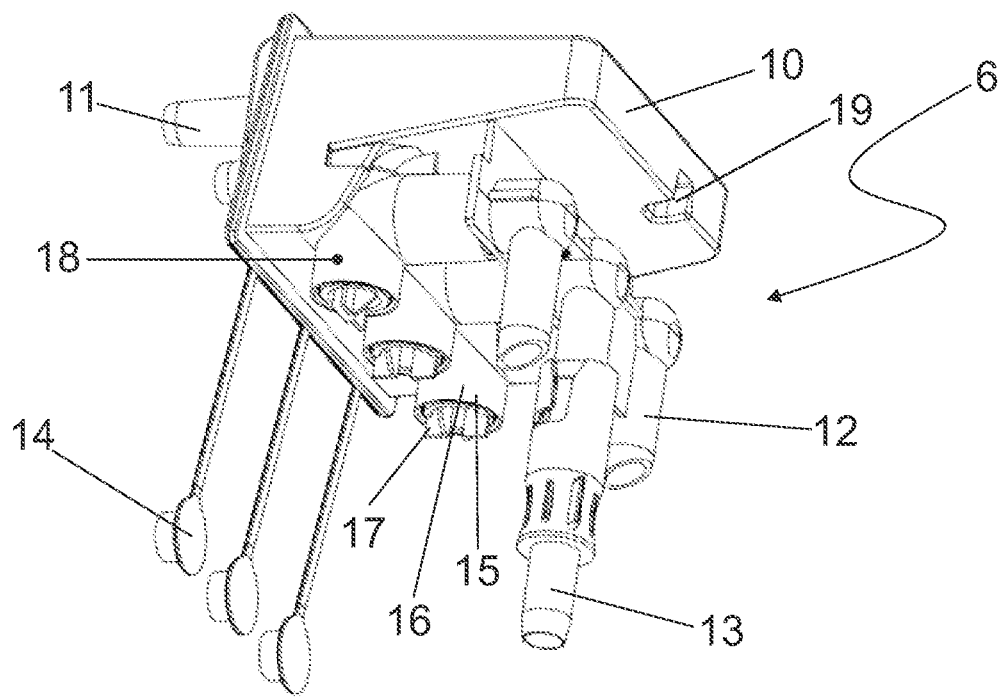
FIGS. 6a and 6b show a manifold in a perspective view.

FIG. 6a shows a manifold 6 in the apparatus 1. The manifold 6 comprises a housing 10, patient ports 11 for connecting a patient tube and ports 12 for collection containers. In FIG. 6a, one of the ports 12 is provided with a coupling 13 for a collection container tube in order to illustrate the use of the coupling 13. There are also caps 14 for closing the patient ports 11. Each patient port 11 is provided with a no-return valve. In practice, there is a thin plastic tube surrounding the patient port 11 inside the housing 10. The plastic tube is open only when the pressure inside the thin plastic tube is higher than around it.

Each port 12 is provided with a valve 15. The valve 15 comprises a cylinder 16 provided with a hole in which is a rotatable bar having a U shaped notch in its head. When the bar is rotated the valve 15 closes or opens depending on the fact whether the hole and the notch are on the same line, i.e. the port 12 opens when the notch is parallel to the hole and the port shuts off when the notch is divergent to the hole. Alternatively, the valve 15 may comprise two cylinders provided with holes within each other. When the holes of the cylinders are on the same line the valve 15 is open.

The rotatable bar comprises a form 17 to which an axle of an actuator, such as a motor 7, grips. Each valve 15 has an actuator which rotates the valves 15 according to the parameters entered by the user.

When liquid is collected from the patient a tube is connected to the patient port 11 and the collection container tube is connected to the port 12 by the coupling 13. The fluid enters first to the housing 10 and after that it flows through one port 12 which is open to a collection container.

After the suction is interrupted there is a possibility that liquid remains in the collection container tube. Further, negative pressure continues to prevail in the tube and in the collection container. In order to remove the fluid in the tube and return the atmospheric pressure in the collection container, the manifold 6 may comprise by-pass channels 18 in the ports 12 for the collection container tubes. The channel 18 is open only when the port 12 is closed by the valve 15.

The manifold 6 may also comprise a by-pass channel 19 in the housing 10 of the manifold 6. There is a gasket between the housing 10 and the channel 19. The negative pressure prevailing in the manifold 6 can be measured from the channel 19 by connecting the channel 19 to a pressure sensor. The measured negative pressure shows the pressure exerted to the patient and indicates if there is a blockage in the system.

Figure 6B:
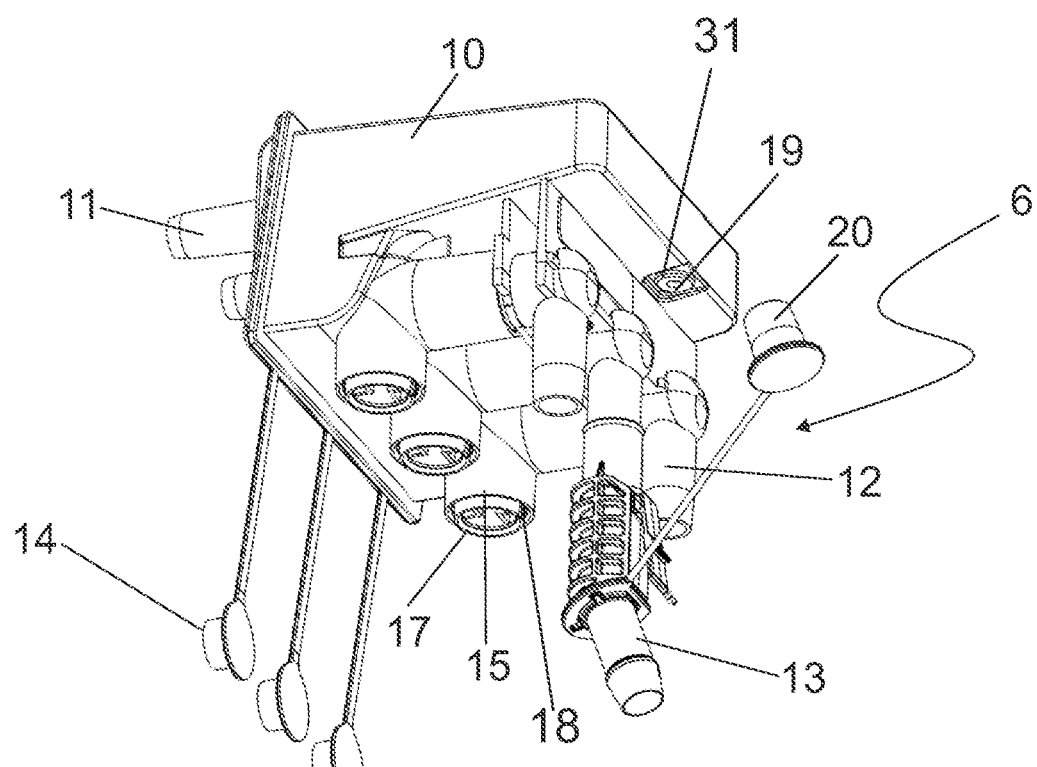

FIG. 6b shows another example of a manifold 6 in the apparatus 1. Basically the manifold 6 has the same structure as in FIG. 6a. However, each port 12 for the collection container tube may comprise a valve 15 comprising two cylinders provided with holes within each other. When the holes are on the same line the valve is open and when the holes are not on the same line the valve is closed. The manifold 6 may be provided with a no-return valve 31 in the beginning of the channel 19 which prevents liquid for entering into the channel 19. The downstream end of the coupling 13 can be closed by a cap 20 after the collection container tube is released from the coupling 13.

Figure 6C:
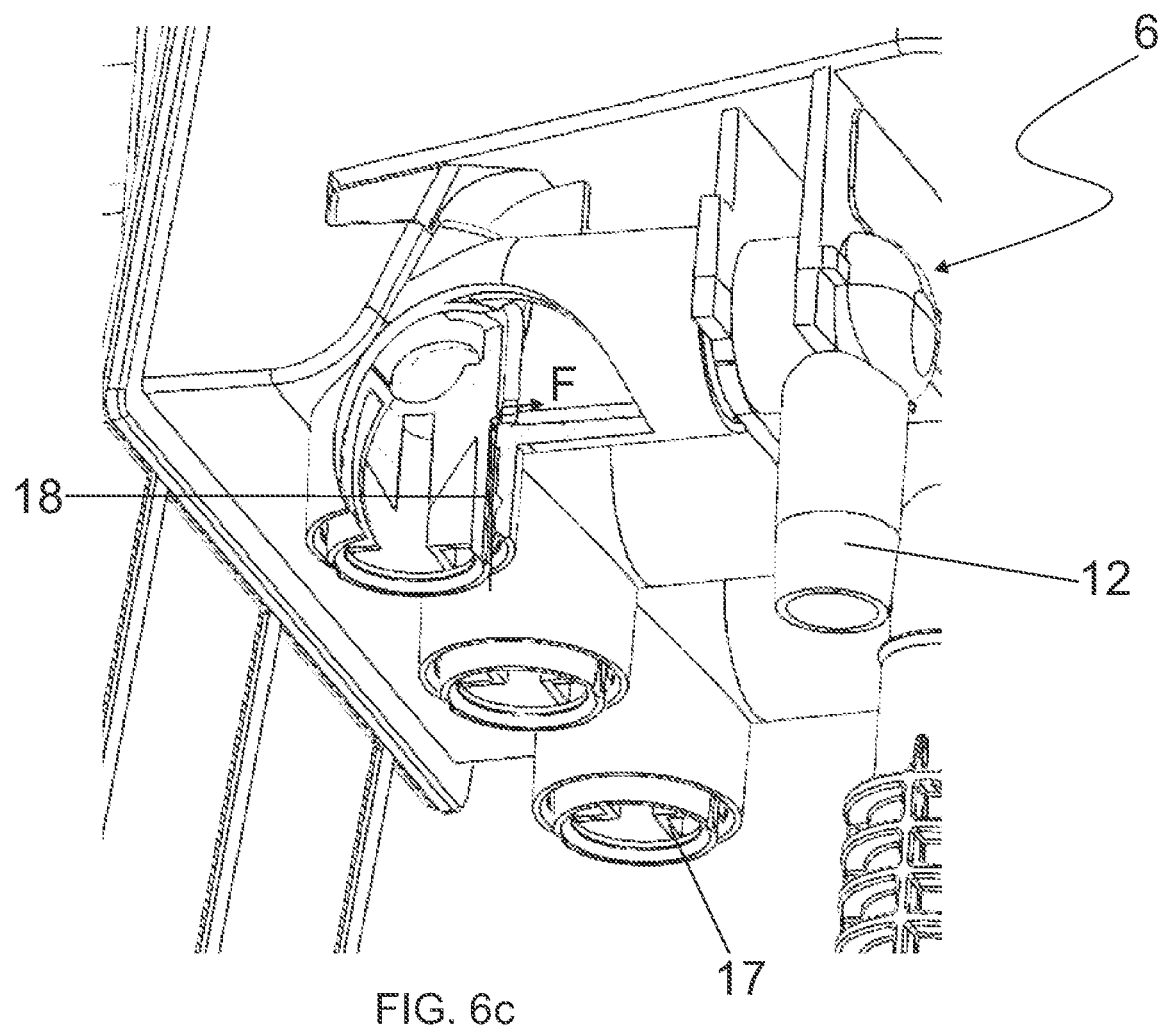
FIGS. 6c and 6d show partial magnifications of the manifold of FIG. 6b.

FIG. 6c shows a partial magnification of a manifold of FIG. 6b. The valve 15 is closed and air flows in the by-pass channel 18. The air flow in the by-pass channel 18 is denoted by arrow F.

Figure 6D:
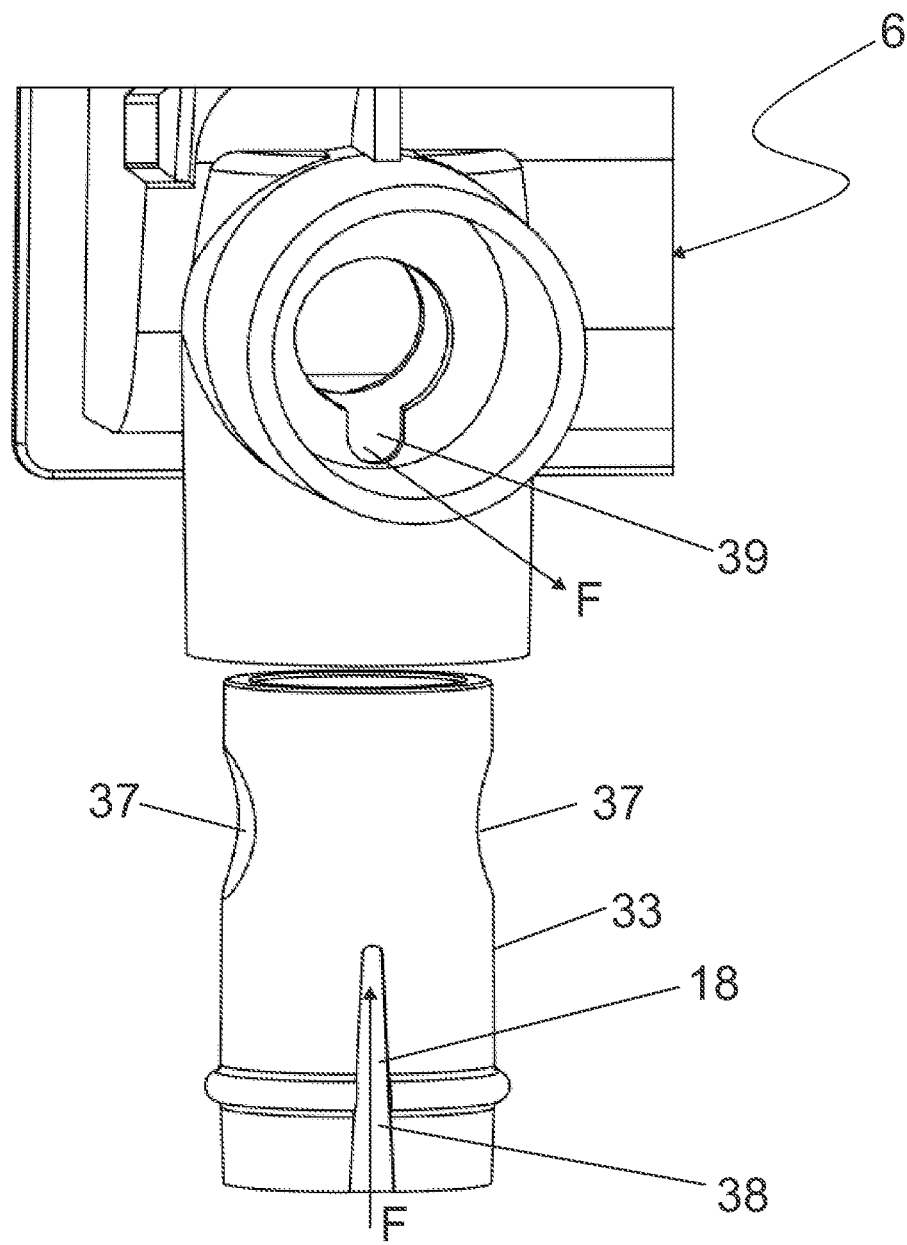

FIG. 6d shows a partial magnification of a manifold of FIG. 6b. The inner cylinder 33 of the valve 15 is shown as an exploded view, i.e. the inner cylinder 33 has been taken out from its normal place which is inside the outer cylinder. The inner cylinder 33 comprises the holes 37 and a first groove 38 which forms the first part of the by-pass channel 18. The second part of the by-pass channel 18 is a second groove 39. When the inner cylinder 33 is inside the outer cylinder and the valve 15 is closed, the air flow F in the by-pass channel 18 advances from the first groove 38 to the second groove 39.

Figure 7A:
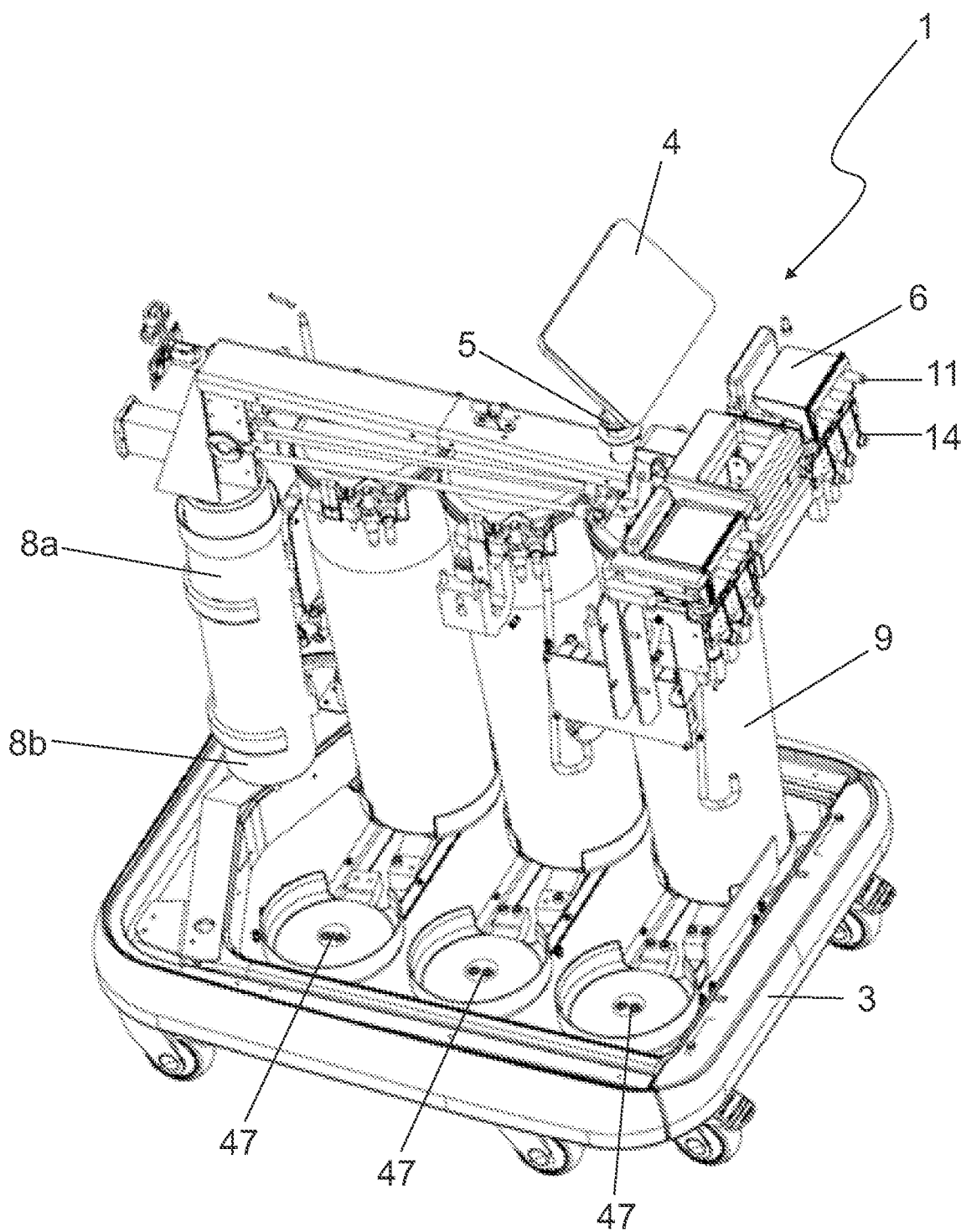
FIGS. 7a to 7c show an apparatus for collecting fluid from a patient in a perspective view.

FIG. 7a shows an apparatus 1 for collecting liquid from a patient. Some of the canisters 9 are removed so that one can see under the canisters 9. There is a strain gauge transducer 47 under each canister 9. The electrical resistance of the strain gauge transducer 47 varies due to the load that is exerted to the transducer 47. On the basis of the resistance the weight of the collection container, i.e. the canister 9 or the collection liner 21 can be determined.

Figure 7B:
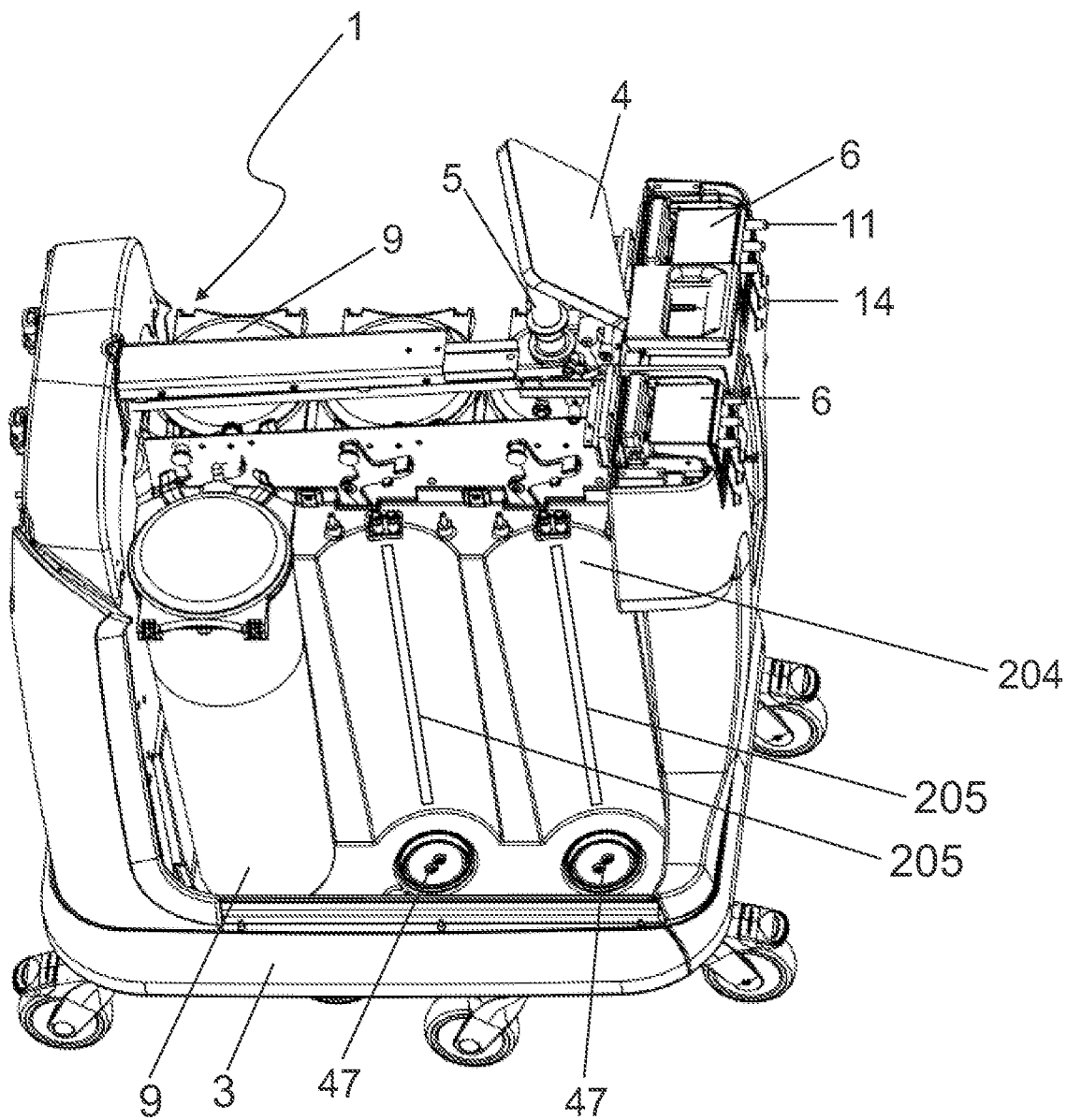

FIG. 7b shows one variation of the apparatus 1 in FIG. 7. The apparatus 1 comprises a separation wall 204. Connections for docking the canister 9 onto the movable cart 3 of the apparatus 1 are behind the separation wall 204.

The separation wall 204 is provided with an illumination device 205 at each canister 9. The illumination device 205 may be a LED stripe. Each illumination device may be controlled separately as to the light intensity or switching on/off.

Figure 7C:
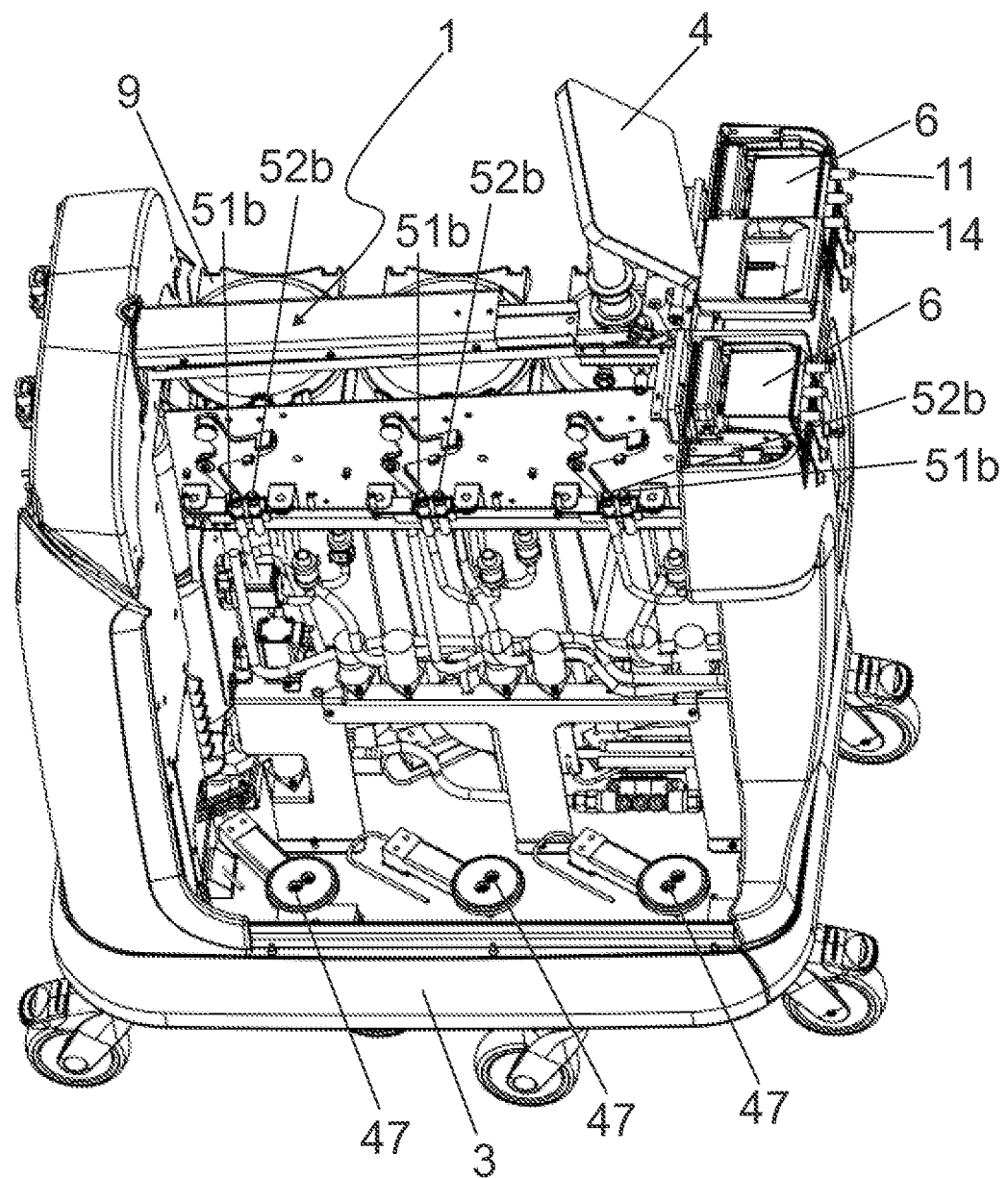

FIG. 7c shows the apparatus 1 of FIG. 7b without the separation wall 204, thus revealing the parts behind the separation wall 204.

Figure 7D:
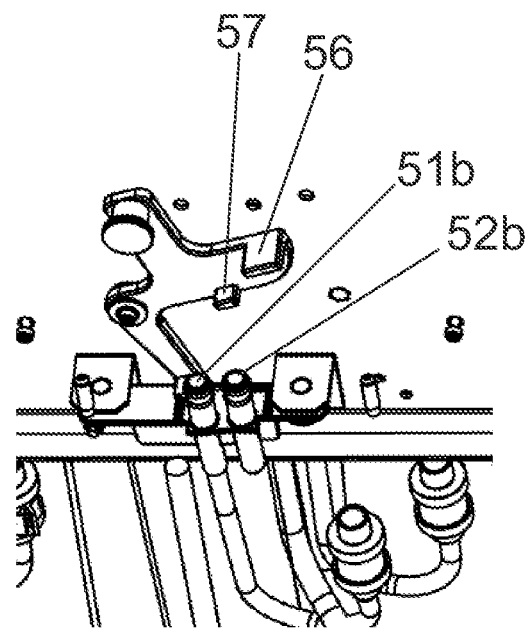
FIGS. 7d to 7g show partial magnifications of details in the apparatus of FIGS. 7a to 7c.

FIG. 7d shows a partial magnification of a detail in the apparatus of FIGS. 7a to 7c. The vacuum port 51 is due to connect to the channel 51b and the channel 52 for the solidifying agent is due to connect to the channel 52b. The channels 51b and 52b float in respect of the body of the apparatus 1. The floating connection makes it possible that the canister 9 moves freely and therefore, it is possible to weigh the canister 9 reliably.

The floating connection can be locked in its place when the canister 9 is changed by moving a docking lever 58 to a prescribed locking position. The docking lever 58 may be replaced by another suitable device, such as a latch or like. In this position, the canister 9 can be attached and detached but the collection liner 21 cannot be used. Once the canister 9 is attached, the floating connection can be resumed by moving the docking lever 58 to a prescribed floating position. In this position the collection liner 21 can be attached to the canister 9 but the canister 9 cannot be detached (for further details see FIGS. 7e to 7g).

The channel 51b may comprise a flow meter measuring a flow value and a second pressure sensor measuring a second pressure value. A first pressure sensor measures a first pressure value which corresponds to the pressure value inside the manifold 6. The pressure difference of the first pressure value and the second pressure value is calculated. The flow value has a predetermined range for each pressure difference. If the flow value is under the predetermined range compared to the predetermined range corresponding the pressure difference in question there is a blockage. If the flow value is over the predetermined range compared to the predetermined range corresponding the pressure difference in question there is a leak.

Figure 7E:
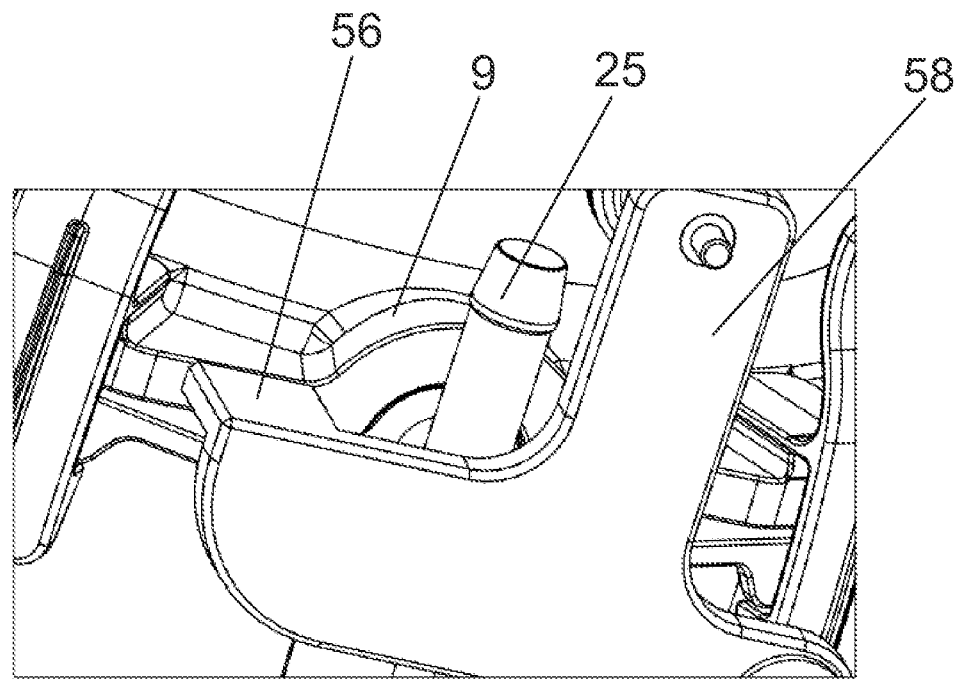

FIG. 7e shows a further detail of the floating connection of the canister 9. The docking lever 58 comprises a stopper 56 which prevents removing the canister 9.

Figure 7F:
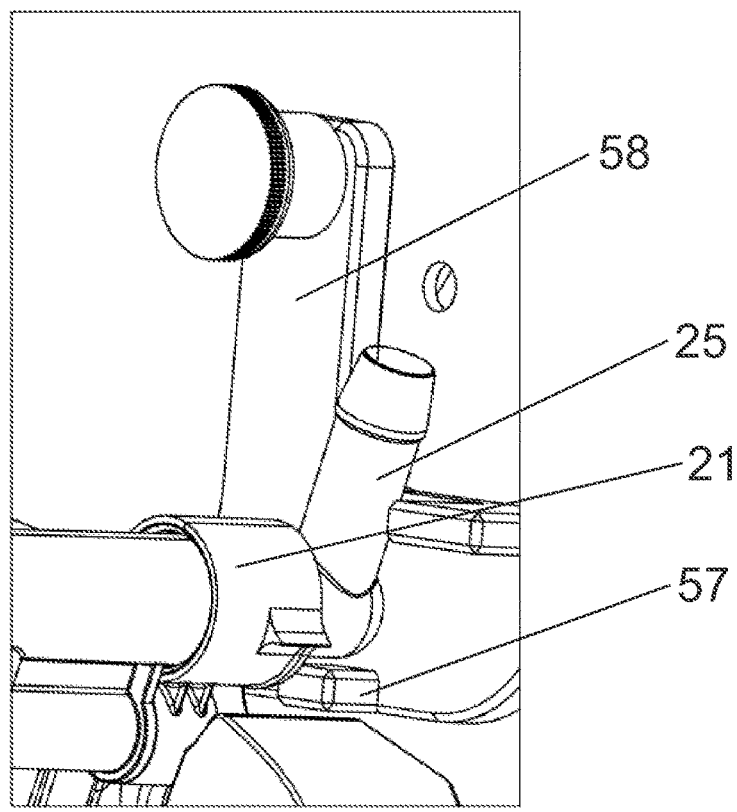
Figure 7G:
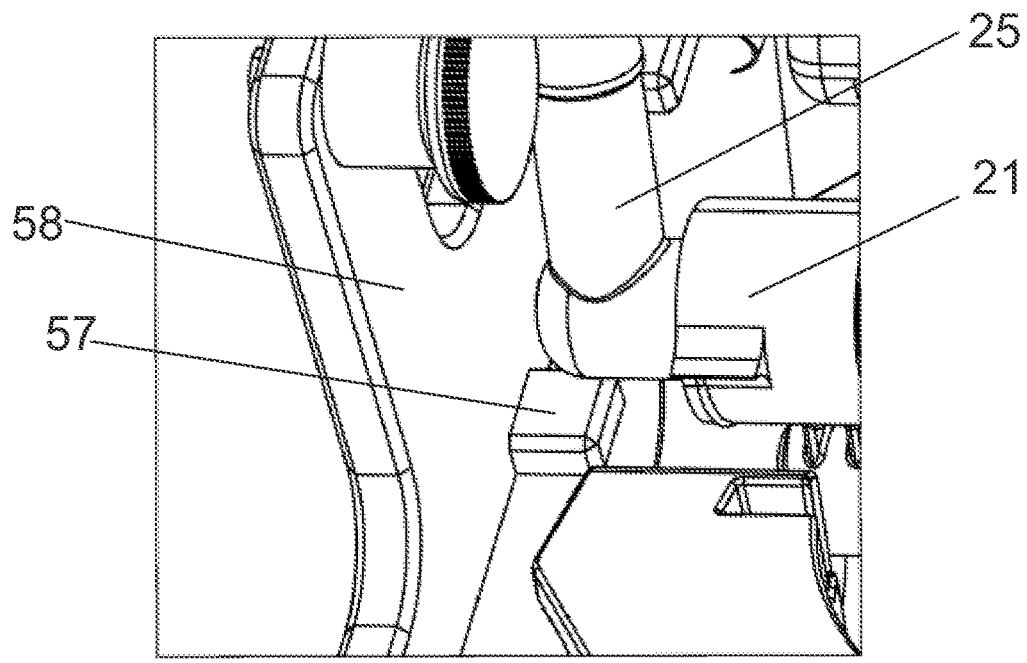

FIGS. 7f and 7g show another further detail of the floating connection of the canister 9. The docking lever 58 comprises a retainer 57 which prevents putting the collection liner 21 into its place.

Figure 8A:
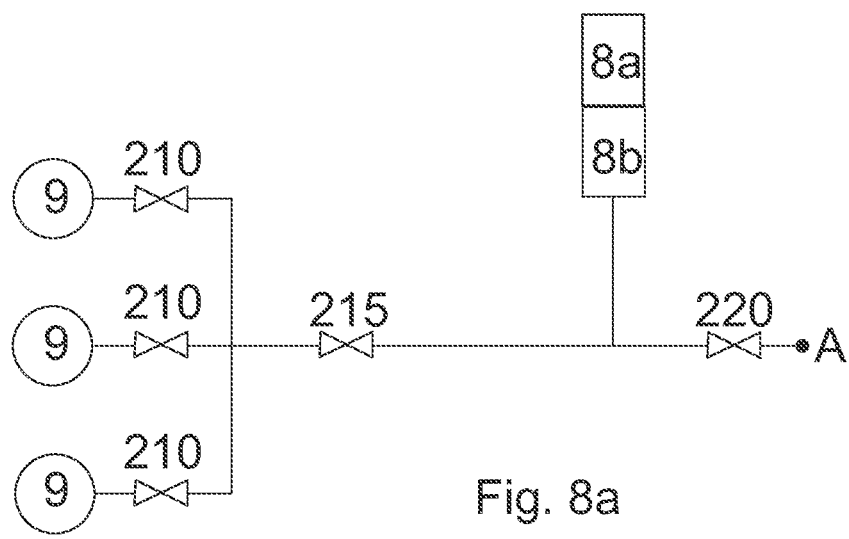
FIG. 8a shows a schematic view of a system for feeding solidifying agent.

FIG. 8a shows a schematic view of a system for feeding solidifying agent or another additive. There are three valves regulating the formation of the solidifying agent portion, namely the first valve 210, the second valve 215 and the third valve 220. The third valve 220 is in contact with ambient air A. Between the second valve 215 and the third valve 220 there is the solidifying agent cartridge 8a and a reservoir 8b which opens into a tube leading to the collection container 9. In the beginning the first valve 210 and the third valve 215 are closed. The second valve 215 is partially open. When the first valve 210 is opened the vacuum starts to draw the solidifying agent out of the reservoir 8b so that a portion of the solidifying agent is formed between the second valve 215 and the third valve 220. In the next step, the first valve 210 and the third valve 220 are open and the second valve 215 is still partially open. Air flows from the third valve 220 which stops the flow of the solidifying agent and compacts the portion of the solidifying agent against the second valve 220.

In the following step all the valves are open. The portion of the solidifying agent is shot then into the collection container 9, thus solidifying the liquid in the collection container. After the portion is shot, the second valve 215 and the third valve 220 are closed in such a manner that the second valve 215 remains partially open as in the beginning of the process. The first valve 210 is also eventually closed and the cycle to form the portion of the solidifying agent starts all over again.

Figure 8B:
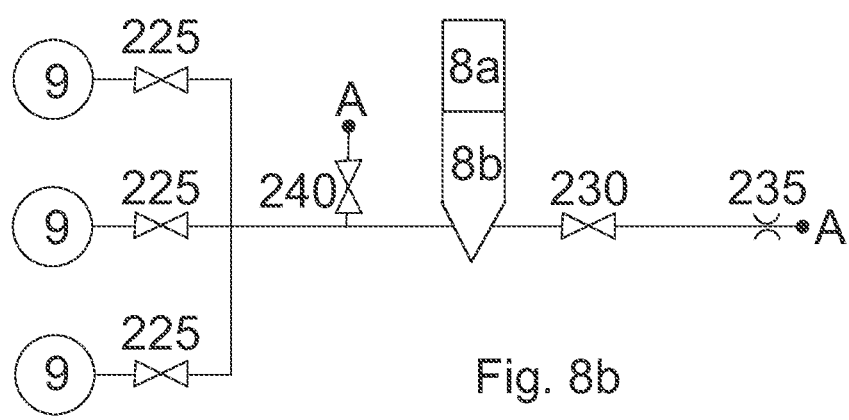
FIG. 8b shows a schematic view of another system for feeding solidifying agent.

FIG. 8b shows a schematic view of another system for feeding solidifying agent or another additive. There are at least two valves, namely a liner valve 225 and an air valve 230, which take part in giving out the solidifying agent. The liner valve 225 is near to the collection container 9. The reservoir 8b receiving solidifying agent from the cartridge 8a is between the air valve 230 and the liner valve 225. The pipe of the solidifying agent pipeline, which passes through the reservoir 8b, may work as an ejector. Such an alternative is described in connection with FIG. 8c.

The liner valve 225 and the air valve 230 are open when the solidifying agent is distributed. The solidifying agent pipeline is in contact with ambient air A through the air valve 230 and it is in contact with vacuum through the liner valve 225. The pipe beyond the air valve 230 may be choked at 235 in order to adjust the balance between ambient air and powder flowing in the pipe.

There may be a flush valve 240 between the reservoir 8b and the liner valve 225. The flush valve 240 is opened at the end of the powder distribution when the air valve 230 has been closed. The aim of the flush valve 240 is that the flush valve 240 opens access to ambient air A and the air flow cleans the pipe from the powder residuals.

Figure 8C:
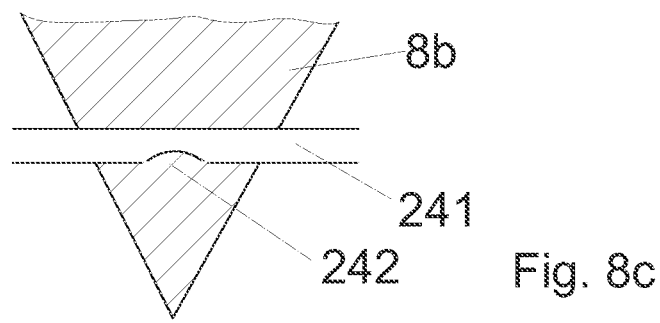
FIG. 8c shows a detail of FIG. 8b as a cross-sectional view.

FIG. 8c shows a detail of FIG. 8b. The pipe 241, which passes through the reservoir 8b, works as an ejector. The lower part of the reservoir 8b may have a shape of an inverted cone as shown in FIGS. 8b and 8c. The pipe 241 has an opening 242 through which air flow grabs the solidifying agent. The opening 242 is on the underside of the pipe 241 because under the pipe 241 the powder is loose and easily movable.

Figure 9:
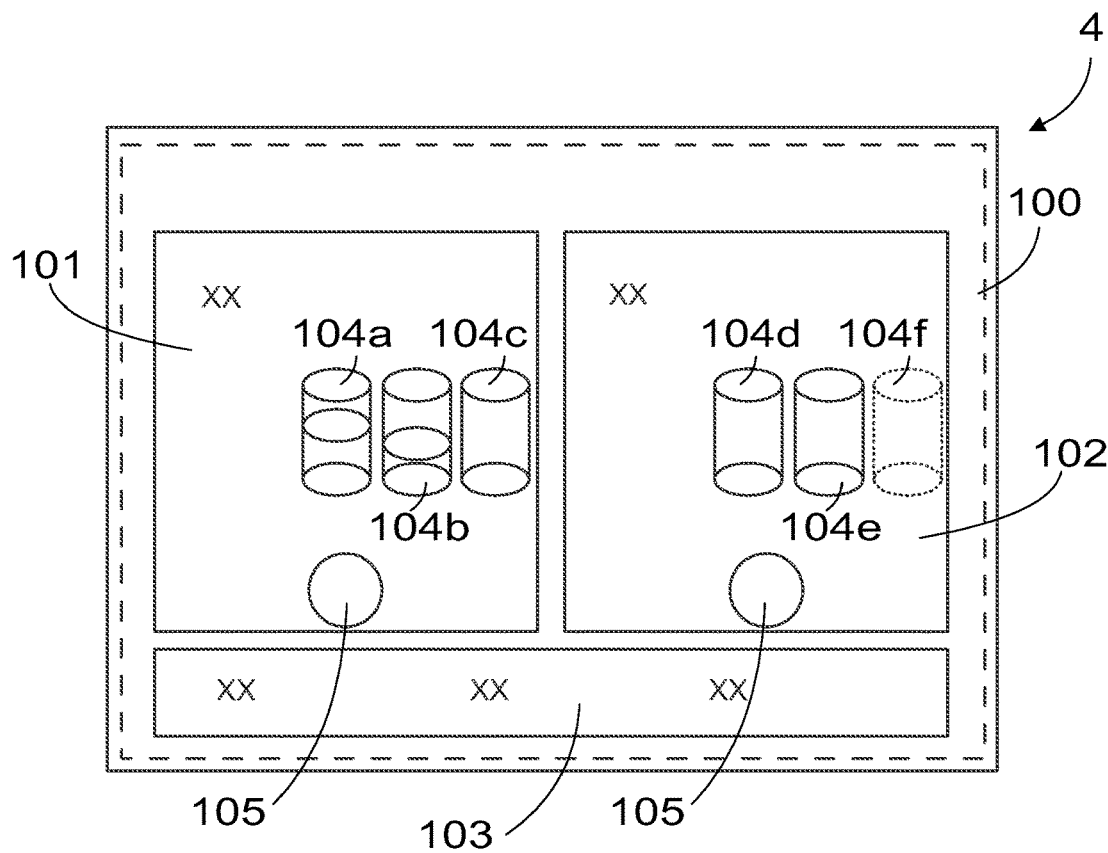
FIG. 9 shows schematically a graphical user interface for an apparatus for collecting liquid from a patient.

FIG. 9 illustrates schematically a graphical user interface 100 for an apparatus for collecting liquid from a patient. The graphical user interface may comprise a display unit 4 and/or different selection means, such as buttons, mouse, joystick and/or touch screen, with which the user may enter input through the graphical user interface 100 for the control unit 2. Naturally, the touch screen may be integrated to the display unit 4. The display unit 4 may comprise one or several display screens.

The graphical user interface 100 for an apparatus for collecting liquid from a patient may comprise at least one first user interface element 101 configured to display on a display unit 4 information related to at least one, preferably at least two, first collection containers 9 connected to a first suction channel XX, at least one second user interface element 102 configured to display on the display unit 4 information related to at least one, preferably at least two, second collection containers 9 connected to a second suction channel, and a third user interface element 103 configured to display on the display unit 4 information regarding liquid collected from the patient to at least one of the collection container 9 such as the amount of liquid collected from the patient to at least one of the collection containers. According to an embodiment, the third user interface element 103 is configured to display on the display unit 4 the total amount of liquid collected from the patient to the collection containers 9. According to an embodiment, the third user interface element 103 is further configured to display on the display unit 4 information regarding the liquid provided to the patient, such as the amount of liquid provided to the patient; and/or the difference between the amount of liquid provided to the patient and the amount of liquid collected from the patient.

According to an embodiment, the first interface element 101 and the second interface element 102 may be configured to display a graphical representation 104a-104f of each one of the collection containers 9. Thus, one graphical representation of a collection container 104a-104f may in each case represent one of the collection containers 9, respectively.

According to an embodiment, the graphical interface 100 may be configured to receive input from a user in the form of the user affecting any one of the graphical representations 104a-104f of the collection containers 9. The affecting may comprise pointing a graphical representation 104a-104f, touching a graphical representations 104a-104f, hovering over a graphical representation 104a-104f and/or any other manner of affecting a graphical user interface known as such.

The graphical interface 100 may be configured to select the collection container 9, the graphical representation 104a-104f of which the user has affected, for collecting fluid from the patient, in response to the input from the user. In other words, the graphical user interface 100 may send a request for the control unit 2 to connect the selected collection container 9 to a corresponding suction channel in response to the user affecting the graphical representation 104a-104f of the collection container 9.

According to an embodiment, the graphical user interface 100 may be configured to select the appearance of each one of the graphic representations 104a-104f of the collection containers 9 in such a manner that a difference appearance is selected for a collection container currently selected, a collection container selectable for collecting fluid from the patient, and a collection container not ready for collecting liquid from the patient. For example, a different colour, different thickness and/or transparency of lines and filling used for showing a collection container 9 on the display unit 4 may be selected by the graphical user interface 100 and/or the control unit 2 based on whether the collection container 9 is a collection container currently selected, a collection container selectable for collecting fluid from the patient, and a collection container not ready for collecting fluid from the patient.

According to an embodiment, the graphical user interface 100 may be configured to select the appearance of each one of the graphic representations 104a-104f of the collection containers 9 to visually show the degree of filling of the collection container 9 in question. For example, the graphical representation 104a-104f may display an illustration of a collection container filled to a degree of filling corresponding to the degree of filling of the actual, corresponding collection container 9.

According to an embodiment, the graphical user interface 100 may further comprise a selection element 105 for starting collection of fluid from the patient to one of said collection containers 9. The graphical user interface 100 may then be configured to receive input from a user in the form of the user affecting the selection element 105 for starting collection of liquid. The graphical user interface 100 may be configured to send a request for starting the collection of liquid from the patient to the selected collection container 9 to a control unit 2 in response to the user affecting the selection element 105 for starting collection of liquid on the graphical user interface 100. The graphical user interface 100 may be configured to only process the input from the user affecting the selection element 105 and to send the request to the control unit 2 if at least one of the collection containers 9 is ready for collecting liquid from the patient. According to an embodiment, the graphical user interface 100 may comprise at least one selection element 105 related to the first user interface element 101 and at least one selection element 105 related to the second user interface element 102, whereby each selection element 105 may be configured to send the request to the control unit 2 to start collecting fluid from the patient through the corresponding suction channel to one of the collection containers 9 that are related to the corresponding user interface element 101, 102.

According to an aspect, a method in connection with a graphical user interface for an apparatus for collecting liquid from a patient comprises steps needed for executing at least one of the functions described in connection with the graphical user interface 100. Preferably, the method comprises a combination of steps needed for executing at least two of the functions described in connection with the graphical user interface 100.

The control unit 2 may comprise a computer, a programmable logic or a programmable microprocessor, for example. The control unit 2 may be configured to cause display of at least one graphical user interface 100 as described above.

The apparatus for collecting liquid from a patient may further comprise at least one memory comprising program code comprising one or more modules, programs or sets of instructions stored in the memory for running operations. In different embodiments, the program code may comprise e.g. a system program, an installable application, an application plugin, an Internet browser or any other piece of computer program code.

According to an aspect, computer code for carrying out at least some of the above-illustrated features may be provided. According to another aspect, the memory and computer program code may be configured to cause the apparatus for collecting liquid from a patient to carry out at least some of the graphical user interface elements 101, 102, 103, 104 and 105, and related features illustrated in connection with FIGS. 1 to 9.

Figure 10:
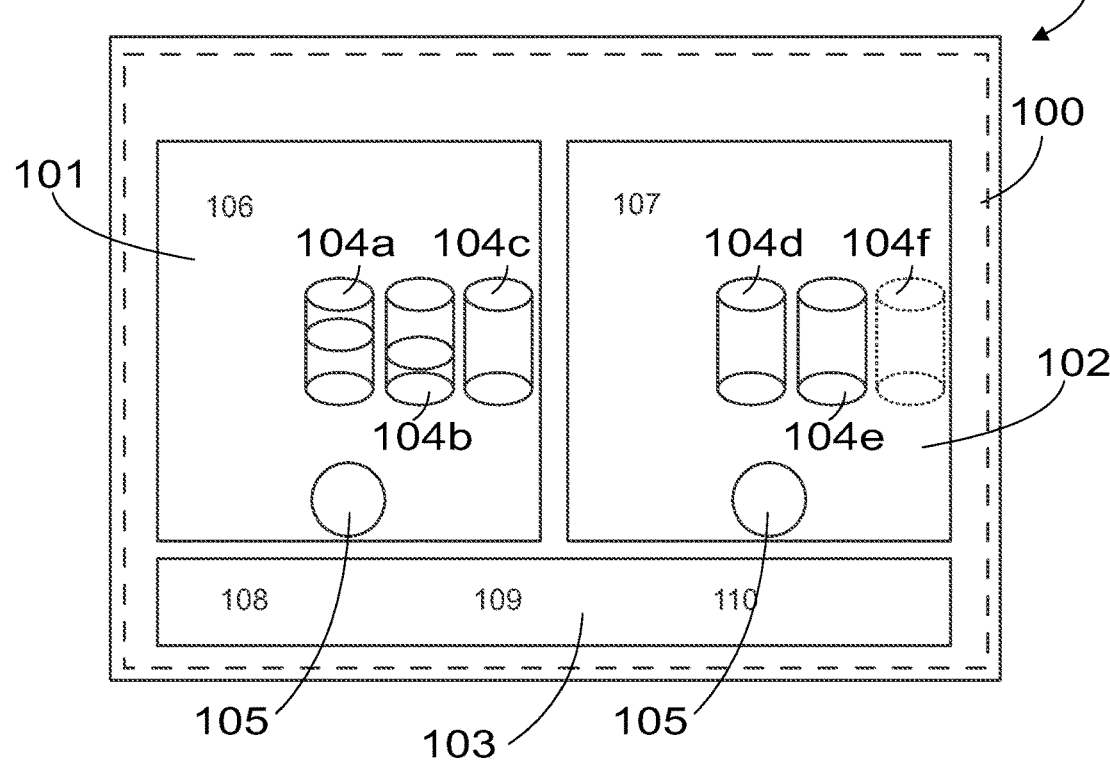
FIG. 10 shows an example of a graphical user interface.

FIG. 10 shows an example of one possible graphical interface 100. The first user interface element 101 shows information about suction channel A and the second user interface element 102 shows information about suction channel B. The collection containers 104a-104c which are joined to the suction channel A are illustrated on the first interface element 101 and the collection containers 104d-104f which are joined to the suction channel B are illustrated on the first interface element 102. The vacuum level of suction channel A can be read from a scale 106 and the vacuum level of suction channel B can be read from a scale 107.

The third user interface element 103 shows in the section 108 the amount of liquid used for irrigation. The section 109 shows the amount of liquid that has been collected from the operation site. The section 110 shows the balance between the readings on the sections 108 and 109.

The main processing included in the display unit 4a controls the display, audio and touch screen. It communicates with the control unit 2 controller over the USB bus. The cart 3 has its own controller communicating with the control unit 2. The main processor, the control unit controller and the cart controller have their own software, memories and peripherals.

The invention claimed is:

1. An assembly for collecting fluid during a medical or a surgical operation, the assembly comprising:
    a canister having an openable lid and a collection liner having a closed bag portion and an inlet for a collection container tube, the inlet having a first end and a second end, which opens into the bag portion and having a no-return valve, the bag portion being configured to be placed inside the canister;
    the first end of the inlet for a collection container tube extending from between an edge of the canister and an edge of the lid to outside of the canister when the lid is closed;
    the no-return valve being configured to be open only when pressure inside the valve is higher than around it; and
    the no-return valve having first and second films one upon the other, the first and second films each having an upper edge, a lower edge and side edges in such a manner that the upper edges of the films are joined to the second end of the inlet, the side edges of the first film are joined to the respective side edges of the second film by seams, and the lower edges of the films are not joined together.

2. The assembly according to claim 1, wherein the collection liner is configured to be engaged to a vacuum through the canister.

3. The assembly according to claim 1, wherein the lid comprises:
    a gasket.

4. The assembly according claim 1, wherein the lid is configured to be detachable from the canister.

5. The assembly according to claim 1, wherein the lid comprises:
    at least one latch.

6. The assembly according claim 1, wherein the lid comprises:
    curved guides inside the lid.

7. The assembly according to claim 6, wherein the guides are concentric.

8. The assembly according to claim 2, wherein the lid comprises:
    a gasket.

9. The assembly according claim 8, wherein the lid is configured to be detachable from the canister.

10. The assembly according to claim 9, wherein the lid comprises:
    at least one latch.

11. The assembly according claim 10, wherein the lid comprises:
    curved guides inside the lid.

12. The assembly according to claim 11, wherein the guides are concentric.

* * * * *